United States Patent
Holmes et al.

(10) Patent No.: US 9,566,352 B2
(45) Date of Patent: Feb. 14, 2017

(54) METHODS AND COMPOSITIONS FOR INHIBITING VIRAL ENTRY INTO CELLS

(75) Inventors: Michael C. Holmes, Oakland, CA (US); Jianbin Wang, San Ramon, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 140 days.

(21) Appl. No.: 13/245,702

(22) Filed: Sep. 26, 2011

(65) Prior Publication Data
US 2012/0093787 A1    Apr. 19, 2012

Related U.S. Application Data

(66) Substitute for application No. 61/404,063, filed on Sep. 27, 2010.

(51) Int. Cl.
| | |
|---|---|
| A61K 48/00 | (2006.01) |
| C07K 14/00 | (2006.01) |
| C12N 5/07 | (2010.01) |
| A61K 38/16 | (2006.01) |
| C07K 14/005 | (2006.01) |
| A61K 35/15 | (2015.01) |
| A61K 35/17 | (2015.01) |
| A61K 35/30 | (2015.01) |
| A61K 35/545 | (2015.01) |

(52) U.S. Cl.
CPC .............. *A61K 48/005* (2013.01); *A61K 35/15* (2013.01); *A61K 35/17* (2013.01); *A61K 35/30* (2013.01); *A61K 35/545* (2013.01); *A61K 38/162* (2013.01); *C07K 14/005* (2013.01); *C07K 2319/32* (2013.01); *C12N 2740/16033* (2013.01); *C12N 2740/16122* (2013.01)

(58) Field of Classification Search
CPC ...................... A61K 47/48776; C07K 2319/00; G01N 2333/726; G01N 33/569; G01N 33/586
See application file for complete search history.

(56) References Cited

U.S. PATENT DOCUMENTS

| | | |
|---|---|---|
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Cas et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,153,949 B2 | 12/2006 | Kim et al. |
| 7,163,824 B2 | 1/2007 | Cox, III et al. |
| 7,253,273 B2 | 8/2007 | Collingwood |
| 7,262,054 B2 | 8/2007 | Jamieson et al. |
| 7,361,635 B2 | 4/2008 | Miller et al. |
| 2003/0026791 A1* | 2/2003 | Humeau et al. ........... 424/93.21 |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0123563 A1* | 6/2005 | Doranz et al. ............. 424/204.1 |
| 2005/0208489 A1 | 9/2005 | Carroll et al. |
| 2005/0267061 A1 | 12/2005 | Martin |
| 2006/0063231 A1 | 3/2006 | Li et al. |
| 2006/0188987 A1 | 8/2006 | Guschin et al. |
| 2007/0134796 A1* | 6/2007 | Holmes et al. ............... 435/455 |
| 2007/0212349 A1 | 9/2007 | Dimitrov et al. |
| 2007/0218528 A1 | 9/2007 | Miller et al. |
| 2008/0131962 A1 | 6/2008 | Miller et al. |
| 2008/0159996 A1 | 7/2008 | Ando et al. |
| 2008/0299580 A1 | 12/2008 | DeKelver et al. |
| 2009/0068164 A1 | 3/2009 | Segal et al. |
| 2009/0117617 A1* | 5/2009 | Holmes et al. ............. 435/69.7 |
| 2009/0263900 A1 | 10/2009 | Dekelver et al. |
| 2010/0291048 A1 | 11/2010 | Holmes et al. |

(Continued)

FOREIGN PATENT DOCUMENTS

| | | |
|---|---|---|
| GB | 2338237 | 12/1999 |
| WO | WO 95/19431 A1 | 7/1995 |

(Continued)

OTHER PUBLICATIONS

Remy et al, Zinc-Finger Nucleases: a Powerful Tool for Genetic Engineering of Animals. Transgenic Research. 2010. 19:363-371.*
Wolkowicz et al, A Random Peptide Library Fused to CCR5 for selection of Mimetopes Expressed on the Mammalian Cell Surface via Retroviral Vectors. The Journal of Biological Chemistry, 2005. 280(15):15195-15201.*
Ylisastigui et al. Effectof RANTES on the Infection of Monocyte-derived Primary Macrophages by Human Immunodeficiency Virus Type 1 and Type 2. Biomed & Pharmacotherapy, 1998. 52:447-53.*
Berger et al. Chemokine Receptors as HIV-1 Coreceptors: Roles in Viral Entry, Tropism, and Disease. Annual Reviews in Immunology, 1999. 17:657-700.*
Hermann et al. Protein Scaffold and Expression Level Determine Antiviral Activity of Membrane-Anchored Antiviral Peptides. Human Gene Therapy, 2009. 325-336.*

(Continued)

*Primary Examiner* — Maria Leavitt
*Assistant Examiner* — Kimberly A Aron
(74) *Attorney, Agent, or Firm* — Pasternak Patent Law; Susan Abrahamson

(57) ABSTRACT

Disclosed herein are methods and compositions for inhibiting viral entry into cells.

7 Claims, 10 Drawing Sheets

(56) References Cited

U.S. PATENT DOCUMENTS

| | | |
|---|---|---|
| 2011/0201055 A1 | 8/2011 | Doyon et al. |
| 2011/0301073 A1 | 12/2011 | Gregory et al. |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 2007/014275 A2 | 2/2007 |
| WO | WO 03/016496 A2 | 2/2008 |
| WO | WO 2008143910 A2 * | 11/2008 |
| WO | WO 2009/042163 A2 | 4/2009 |
| WO | WO 2009/054985 A1 | 4/2009 |
| WO | WO 2010/079430 A1 | 7/2010 |
| WO | 2010/107493 A2 | 9/2010 |

OTHER PUBLICATIONS

Hrobowski et al. Peptide Inhibitors of Dengue Virus and West Nile Virus Infectivity. Virology Journal, 2005. 2:49, 10 pages.*

Beerli, et al., "Engineering Polydactyl Zinc-Finger Transcription Factors," *Nature Biotechnol.* 20:135-141 (2002).

Boch, et al., "Breaking the Code of DNA Binding Specificity of Tal-Type III Effectors," *Science* 326(5959):1509-1512 (2009).

Bonas, et al., "Genetic and Structural Characterization of the Avirulence Gene AVRBS3 From Xanthomonas Campestris PV. Vesicatoria," *Mol. Gen. Genet.* 218(1):127-136 (1989).

Chan, et al., "Core Structure of GP41 From the HIV Envelope Glycoprotein," *Cell* 89(2):263-273 (1997).

Christian, et al., "Targeting DNA Double-Strand Breaks With Tal Effector Nucleases," *Genetics* 186(2):757-761 (2010).

Choo, et al., "Advances in Zinc Finger Engineering," *Curr. Opin. Struct. Biol.*, 10: 411-416 (2000).

Deng, et al., "Identification of a Major Co-Receptor for Primary Isolates of HIV-1," *Nature* 381(6584):661-666 (1996).

Eckert, et al., "Mechanisms of Viral Membrane Fusion and Its Inhibition," *Annu. Rev. Biochem.* 70:777-810 (2001).

Egelhofer, et al., "Inhibition of Human Immunodeficiency Virus Type 1 Entry in Cells Expressing GP41-Derived Peptides," *J. Virol.* 78(2):568-575 (2004).

Etemad-Moghadam, et al., "Envelope Glycoprotein Determinants of Increased Fusogenicity in a Pathogenic Simian-Human Immunodeficiency Virus (SHIV-KB9) Passaged In Vivo," *J. Virol.* 74(9):4433-4440 (2000).

Feng, et al., "HIV-1 Entry Cofactor: Functional CDNA Cloning of a Seven-Transmembrane, G Protein-Coupled Receptor," *Science* 272(5263):872-877.

Gabuzda, et al., "Chemokine Receptors and Mechanisms of Cell Death in HIV Neuropathogenesis," *J Neurovirol.* 6(1):524-32 (2000).

Gupta, et al., "Novel Resistance Mechanism of HIV-1 to Peptide Fusion Inhibitors," *Retrovirology* 3(1):S86 (2006).

Heuer, et al., "Repeat Domain Diversity of AVRBS3-Like Genes in Ralstonia Solanacearum Strains and Association With Host Preferences in the Field," *Appl. Environ. Microbiol.* 73(13):4379-4384 (2007).

Hildinger, et al., "Membrane-Anchored Peptide Inhibits Human Immunodeficiency Virus Entry," *J. Virol.* 75(6):3038-3042 (2001).

Holt, et al., "Human Hematopoietic Stem/Progenitor Cells Modified by Zinc-Finger Nucleases Targeted to CCR5 Control HIV-1 In Vivo," *Nat. Biotechnol.* 28(8):839-47 (2010).

Ingallinella, et al., "Addition of a Cholesterol Group to an HIV-1 Peptide Fusion Inhibitor Dramatically Increases Its Antiviral Potency," *PNAS USA* 106(14):5801-5806 (2009).

Isalan, et al., "A Rapid, Generally Applicable Method to Engineer Zinc Fingers Illustrated by Targeting the HIV-1 Promoter," *Nature Biotechnology* 19(7):656-660 (2001).

Ishikawa, et al., "Development of Functional Human Blood and Immune Systems in NOD/SCID/IL2 Receptor {Gamma} Chain-(Null) Mice," *Blood* 106(5):1565-1573 (2005).

Kim, et al., "Hybrid Restriction Enzymes: Zinc Finger Fusions to FOK I Cleavage Domain," *PNAS* 93(3):1156-1160 (1996).

Kimpel, et al., "Survival of the Fittest: Selection of Vector-Transduced Cells During HIV-1 Replication," *PLoS One* 5(8):e12357 (2010).

Liu, et al., "Different From the HIV Fusion Inhibitor C34, The Anti-HIV Drug Fuzeon (T-20) Inhibits HIV-1 Entry by Targeting Multiple Sites in GP41 and GP120," *J. Biol. Chem.*, 280(12):11259-11273 (2005).

Lusso, et al., "HIV and the Chemokine System: 10 Years Later," *The Embo Journal* 25(3):447-456 (2006).

Moscou, et al., "A Simple Cipher Governs DNA Recognition by TAL Effectors," *Science* 326(5959):1501 (2009).

Munoz-Barroso, et al., "Dilation of the Human Immunodeficiency Virus-1 Envelope Glycoprotein Fusion Pore Revealed by the Inhibitory Action of a Synthetic Peptide From GP41,"*J. Cell Biol.* 140(2):315-323 (1998).

Naider, et al., "Peptides in the Treatment of Aids," *Curr. Opin. Struct. Biol.* 19(4):473-482 (2009).

Naito, et al., "SC29EK, A Peptide Fusion Inhibitor With Enhanced A-Helicity, Inhibits Replication of Human Immunodeficiency Virus Type 1 Mutants Resistant to Enfuvirtide," *Antimicrob. Agents Chemother.* 53(3): 1013-1018 (2009).

Pabo, et al., "Design and Selection of Novel CYS2HIS2 Zinc Finger Proteins," *Ann. Rev. Biochem.* 70:313-340 (2001).

Rockstroh, et al., "Clinical Perspective of Fusion Inhibitors for Treatment of HIV," *J. Antimicrob. Chemother.* 53(5):700-702 (2004).

Schornack, et al., "Gene-For-Gene-Mediated Recognition of Nuclear-Targeted AVRBS3-Like Bacterial Effector Proteins," *J. Plant Physiol.* 163(3):256-272 (2006).

Segal, et al., "Custom DNA-Binding Proteins Come of Age: Polydactyl Zinc-Finger Proteins," *Curr. Opin. Biotechnol.* 12(6):632-637 (2001).

Stoddart, et al., "Albumin-Conjugated C34 Peptide HIV-1 Fusion Inhibitor," *J Biol. Chem.* 283(49):34045-34052 (2008).

Wang, et al., "IL-4 and a Glucocorticoid Up-Regulate CXCR4 Expression on Human CD4+ T Lymphocytes and Enhance HIV-1 Replication," *J. of Leukoc. Biol.* 64(5):642-649 (1998).

Wexler-Cohen, et al., "Membrane-Anchored HIV-1 N-Heptad Repeat Peptides Are Highly Potent Cell Fusion Inhibitors Via an Altered Mode of Action," *Plos Pathog.* 5(7):e1000509 (2009).

Zahn, et al., "Efficient Entry Inhibition of Human and Nonhuman Primate Immunodeficiency Virus by Cell Surface-Expressed GP41-Derived Peptides," *Gene Ther.* 15(17):1210-1222 (2008).

Berkhout et al., "Is There a Future for Antiviral Fusion Inhibitors?," Current Opinion in Virology, 2(1):52-55 (2012).

Henrich et al., "HIV-1 Entry Inhibitors: Recent Development and Clinical Use," Current Opinion in Virology, 3(1):51-57 (2013).

Ingallinella et al., "Addition of a Cholesterol Group to an HIV-1 Peptide Fusion Inhibitor Dramatically Increases Its Antiviral Potency," Proceedings of the National Academy of Sciences, 106(14):5801-5806 (2009).

Jiang et al., "Peptide and Non-Peptide HIV Fusion Inhibitors," Current Pharmaceutical Design, 8(8):563-580 (2002).

Koptezki et al., "Closing Two Doors of Viral Entry: Intramolecular Combination of a Coreceptor- and Fusion Inhibitor of HIV-1," Virology Journal 5(1):56 (2008).

Miyamoto et al., "Development of Small Molecule HIV-1 Fusion Inhibitors: Linking Biolgy to Chemistry," Current Pharmaceutical Design, 19(10):1827-1834 (2013).

Perez et al., "Towards Gene Knock Out Therapy for AIDS/HIV: Targeted Disruption of CCR5 Using Engineered Zinc Finger Protein Nucleases (ZFNS)," Molecular Therapy 13(1):S293 (2006).

(56) References Cited

OTHER PUBLICATIONS

Steffen and Pohlmann, "Peptide-Based Inhibitors of the HIV Envelope Protein and Other Class I Viral Fusion Proteins," Current Pharmaceutical Design, 16(9):1143-1149 and 1151-1152 (2010).
Veazey et al., "Tropism-Independent Protection of Macaques Against Vaginal Transmission of Three Shivs by the HIV-1 Fusion Inhibitor T-1249," Proceedings of the National Academy of Sciences, 105(30):10531-10536 (2008).
Wang et al., "Selection With a Peptide Fusion Inhibitor Corresponding to the First Heptad Repeat of HIV-1 GP41 Indentifies Two Genetic Pathways Conferring Cross-Resistrance to Peptide Fusion Inhibitors Corresponding to the First and Second Heptad Repeats (HR1 and HR2) of GP41," Journal of Virology, 85(24):12929-12938 (2011).
Sadelain, et al., "Safe Harbours for the Integration of New DNA in the Human Genome," Nature Reviews 12:51-58 (2012).

\* cited by examiner

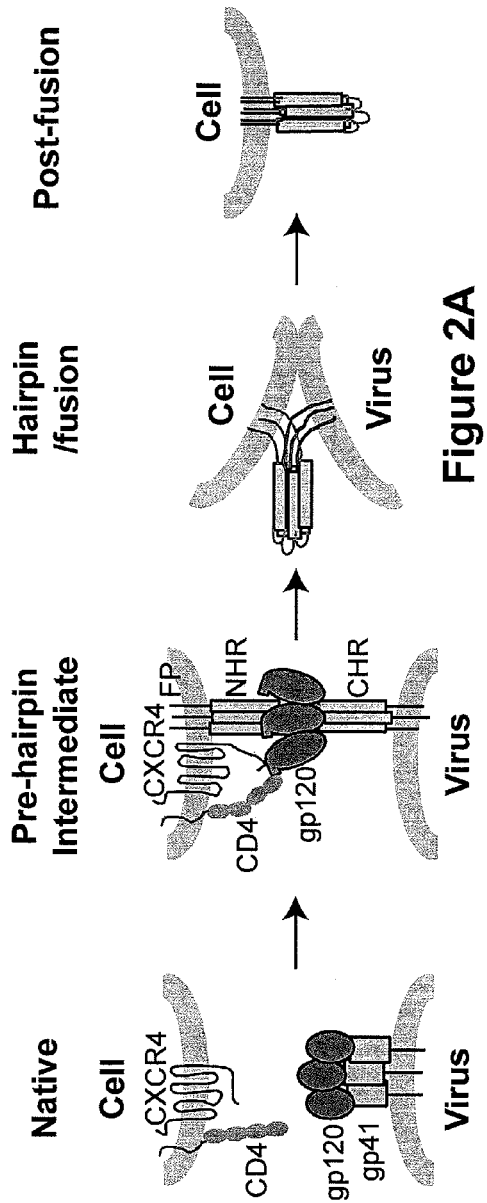
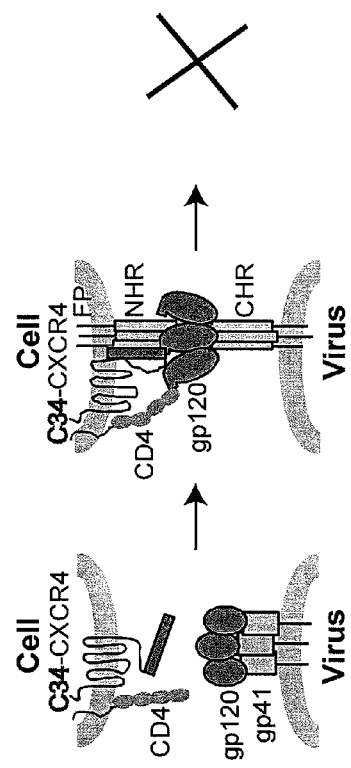

Figure 3

```
WT:       ATATCTGTGACCGCTTCTACCCCAATGACTTGTGGGTGGT
B4-seq1:  ATATCTGTGACCGCTTCTACCC--------GGTGGT
B4-seq2:  ATATCT------------------TGACTTGTGGGTGGT
```

C34 S2 and S10 mutations

| | Position | | Position |
|---|---|---|---|
| C34 | 628- | WMEWDREINNYTSLIHSLIEESQNQQEKNEQELL | -661  (SEQ ID NO:5) |
| C34S2 | 628- | WMEWDREINNATSLIHSLIEEAQNQQEKNEQELL | -661  (SEQ ID NO:8) |
| C34S10 | 628- | AMEADREANNATSLAHSAIEEAQNAQEKAEQALL | -661  (SEQ ID NO:9) |

Figure 6

SEQUENCE LISTING

```
<160> NUMBER OF SEQ ID NOS: 22

<210> SEQ ID NO 1
<211> LENGTH: 40
<212> TYPE: DNA
<213> ORGANISM: Homo sapiens

<400> SEQUENCE: 1
atatctgtga ccgcttctac cccaatgact tgtgggtggt                              40

<210> SEQ ID NO 2
<211> LENGTH: 28
<212> TYPE: DNA
<213> ORGANISM: Homo sapiens

<400> SEQUENCE: 2
atatctgtga ccgcttctac ccggtggt                                          28

<210> SEQ ID NO 3
<211> LENGTH: 21
<212> TYPE: DNA
<213> ORGANISM: Homo sapiens

<400> SEQUENCE: 3
atatcttgac ttgtgggtgg t                                                 21

<210> SEQ ID NO 4
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Trp Met Glu Trp Asp Arg Glu Ile Asn Asn Tyr Thr Ser Leu Ile
1               5                   10                  15

His Ser Leu Ile Glu Glu Ser Gln Asn Gln Gln Glu Lys Asn Glu Gln
            20                  25                  30
```

Glu Leu Leu Leu Lys Thr Met Glu Gly Ile Ser Ile Tyr Thr Ser Asp
            35                  40                  45

Asn Tyr Thr Glu Glu Met Gly Ser Gly Asp Tyr Asp Ser Met Lys Glu
 50                  55                  60

Pro Cys Phe Arg Glu Glu Asn Ala Asn Phe Asn Lys Ile Phe Leu Pro
 65                  70                  75                  80

Thr Ile Tyr Ser Ile Ile Phe Leu Thr Gly Ile Val Gly Asn Gly Leu
                 85                  90                  95

Val Ile Leu Val Met Gly Tyr Gln Lys Lys Leu Arg Ser Met Thr Asp
            100                 105                 110

Lys Tyr Arg Leu His Leu Ser Val Ala Asp Leu Leu Phe Val Ile Thr
            115                 120                 125

Leu Pro Phe Trp Ala Val Asp Ala Val Ala Asn Trp Tyr Phe Gly Asn
130                 135                 140

Phe Leu Cys Lys Ala Val His Val Ile Tyr Thr Val Asn Leu Tyr Ser
145                 150                 155                 160

Ser Val Leu Ile Leu Ala Phe Ile Ser Leu Asp Arg Tyr Leu Ala Ile
                165                 170                 175

Val His Ala Thr Asn Ser Gln Arg Pro Arg Lys Leu Leu Ala Glu Lys
            180                 185                 190

Val Val Tyr Val Gly Val Trp Ile Pro Ala Leu Leu Leu Thr Ile Pro
            195                 200                 205

Asp Phe Ile Phe Ala Asn Val Ser Glu Ala Asp Asp Arg Tyr Ile Cys
    210                 215                 220

Asp Arg Phe Tyr Pro Asn Asp Leu Trp Val Val Val Phe Gln Phe Gln
225                 230                 235                 240

His Ile Met Val Gly Leu Ile Leu Pro Gly Ile Val Ile Leu Ser Cys
                245                 250                 255

Tyr Cys Ile Ile Ile Ser Lys Leu Ser His Ser Lys Gly His Gln Lys
            260                 265                 270

Arg Lys Ala Leu Lys Thr Thr Val Ile Leu Ile Leu Ala Phe Phe Ala
            275                 280                 285

Cys Trp Leu Pro Tyr Tyr Ile Gly Ile Ser Ile Asp Ser Phe Ile Leu
    290                 295                 300

Leu Glu Ile Ile Lys Gln Gly Cys Glu Phe Glu Asn Thr Val His Lys
305                 310                 315                 320

Trp Ile Ser Ile Thr Glu Ala Leu Ala Phe Phe His Cys Cys Leu Asn
                325                 330                 335

Pro Ile Leu Tyr Ala Phe Leu Gly Ala Lys Phe Lys Thr Ser Ala Gln
            340                 345                 350

His Ala Leu Thr Ser Val Ser Arg Gly Ser Ser Leu Lys Ile Leu Ser
            355                 360                 365

Lys Gly Lys Arg Gly Gly His Ser Ser Val Ser Thr Glu Ser Glu Ser
370                 375                 380

Ser Ser Phe His Ser Ser
385                 390

<210> SEQ ID NO 5
<211> LENGTH: 34
<212> TYPE: PRT
<213> ORGANISM: Human immunodeficiency virus 1

<400> SEQUENCE: 5

Trp Met Glu Trp Asp Arg Glu Ile Asn Asn Tyr Thr Ser Leu Ile His
 1               5                  10                  15

```
Ser Leu Ile Glu Glu Ser Gln Asn Gln Gln Glu Lys Asn Glu Gln Glu
            20                  25                  30

Leu Leu

<210> SEQ ID NO 6
<211> LENGTH: 389
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Leu Lys Asp Tyr Gln Val Ser Ser Pro Ile Tyr Asp
            35                  40                  45

Ile Asn Tyr Tyr Thr Ser Glu Pro Cys Gln Lys Ile Asn Val Lys Gln
50                  55                  60

Ile Ala Ala Arg Leu Leu Pro Pro Leu Tyr Ser Leu Val Phe Ile Phe
65                  70                  75                  80

Gly Phe Val Gly Asn Met Leu Val Ile Leu Ile Leu Ile Asn Cys Lys
            85                  90                  95

Arg Leu Lys Ser Met Thr Asp Ile Tyr Leu Leu Asn Leu Ala Ile Ser
            100                 105                 110

Asp Leu Phe Phe Leu Leu Thr Val Pro Phe Trp Ala His Tyr Ala Ala
            115                 120                 125

Ala Gln Trp Asp Phe Gly Asn Thr Met Cys Gln Leu Leu Thr Gly Leu
            130                 135                 140

Tyr Phe Ile Gly Phe Phe Ser Gly Ile Phe Phe Ile Ile Leu Leu Thr
145                 150                 155                 160

Ile Asp Arg Tyr Leu Ala Val Val His Ala Val Phe Ala Leu Lys Ala
                165                 170                 175

Arg Thr Val Thr Phe Gly Val Val Thr Ser Val Ile Thr Trp Val Val
            180                 185                 190

Ala Val Phe Ala Ser Leu Pro Gly Ile Ile Phe Thr Arg Ser Gln Lys
            195                 200                 205

Glu Gly Leu His Tyr Thr Cys Ser Ser His Phe Pro Tyr Ser Gln Tyr
            210                 215                 220

Gln Phe Trp Lys Asn Phe Gln Thr Leu Lys Ile Val Ile Leu Gly Leu
225                 230                 235                 240

Val Leu Pro Leu Leu Val Met Val Ile Cys Tyr Ser Gly Ile Leu Lys
                245                 250                 255

Thr Leu Leu Arg Cys Arg Asn Glu Lys Lys Arg His Arg Ala Val Arg
            260                 265                 270

Leu Ile Phe Thr Ile Met Ile Val Tyr Phe Leu Phe Trp Ala Pro Tyr
            275                 280                 285

Asn Ile Val Leu Leu Leu Asn Thr Phe Gln Glu Phe Phe Gly Leu Asn
290                 295                 300

Asn Cys Ser Ser Ser Asn Arg Leu Asp Gln Ala Met Gln Val Thr Glu
305                 310                 315                 320

Thr Leu Gly Met Thr His Cys Cys Ile Asn Pro Ile Ile Tyr Ala Phe
                325                 330                 335
```

```
Val Gly Glu Lys Phe Arg Asn Tyr Leu Leu Val Phe Gln Lys His
            340                 345                 350

Ile Ala Lys Arg Phe Cys Lys Cys Ser Ile Phe Gln Gln Glu Ala
            355                 360                 365

Pro Glu Arg Ala Ser Ser Val Tyr Thr Arg Ser Thr Gly Gln Glu
    370                 375                 380

Ile Ser Val Gly Leu
385

<210> SEQ ID NO 7
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Trp Met
                20                  25                  30

Glu Trp Asp Arg Glu Ile Asn Asn Tyr Thr Ser Leu Ile His Ser Leu
            35                  40                  45

Ile Glu Glu Ser Gln Asn Gln Gln Glu Lys Asn Glu Gln Glu Leu Leu
        50                  55                  60

Glu Phe Lys Lys Val Val Leu Gly Lys Lys Gly Asp Thr Val Glu Leu
65                  70                  75                  80

Thr Cys Thr Ala Ser Gln Lys Lys Ser Ile Gln Phe His Trp Lys Asn
                85                  90                  95

Ser Asn Gln Ile Lys Ile Leu Gly Asn Gln Gly Ser Phe Leu Thr Lys
                100                 105                 110

Gly Pro Ser Lys Leu Asn Asp Arg Ala Asp Ser Arg Arg Ser Leu Trp
            115                 120                 125

Asp Gln Gly Asn Phe Pro Leu Ile Ile Lys Asn Leu Lys Ile Glu Asp
        130                 135                 140

Ser Asp Thr Tyr Ile Cys Glu Val Glu Asp Gln Lys Glu Glu Val Gln
145                 150                 155                 160

Leu Leu Val Phe Gly Leu Thr Ala Asn Ser Asp Thr His Leu Leu Gln
                165                 170                 175

Gly Gln Ser Leu Thr Leu Thr Leu Glu Ser Pro Pro Gly Ser Ser Pro
            180                 185                 190

Ser Val Gln Cys Arg Ser Pro Arg Gly Lys Asn Ile Gln Gly Gly Lys
        195                 200                 205

Thr Leu Ser Val Ser Gln Leu Glu Leu Gln Asp Ser Gly Thr Trp Thr
210                 215                 220

Cys Thr Val Leu Gln Asn Gln Lys Lys Val Glu Phe Lys Ile Asp Ile
225                 230                 235                 240

Val Val Leu Ala Phe Gln Lys Ala Ser Ser Ile Val Tyr Lys Lys Glu
                245                 250                 255

Gly Glu Gln Val Glu Phe Ser Phe Pro Leu Ala Phe Thr Val Glu Lys
            260                 265                 270

Leu Thr Gly Ser Gly Glu Leu Trp Trp Gln Ala Glu Arg Ala Ser Ser
        275                 280                 285

Ser Lys Ser Trp Ile Thr Phe Asp Leu Lys Asn Lys Glu Val Ser Val
```

-continued

```
                290                 295                 300

Lys Arg Val Thr Gln Asp Pro Lys Leu Gln Met Gly Lys Lys Leu Pro
305                 310                 315                 320

Leu His Leu Thr Leu Pro Gln Ala Leu Pro Gln Tyr Ala Gly Ser Gly
                325                 330                 335

Asn Leu Thr Leu Ala Leu Glu Ala Lys Thr Gly Lys Leu His Gln Glu
            340                 345                 350

Val Asn Leu Val Val Met Arg Ala Thr Gln Leu Gln Lys Asn Leu Thr
        355                 360                 365

Cys Glu Val Trp Gly Pro Thr Ser Pro Lys Leu Met Leu Ser Leu Lys
370                 375                 380

Leu Glu Asn Lys Glu Ala Lys Val Ser Lys Arg Glu Lys Ala Val Trp
385                 390                 395                 400

Val Leu Asn Pro Glu Ala Gly Met Trp Gln Cys Leu Leu Ser Asp Ser
                405                 410                 415

Gly Gln Val Leu Leu Glu Ser Asn Ile Lys Val Leu Pro Thr Trp Ser
            420                 425                 430

Thr Pro Val Gln Pro Met Ala Leu Ile Val Leu Gly Gly Val Ala Gly
        435                 440                 445

Leu Leu Leu Phe Ile Gly Leu Gly Ile Phe Phe Cys Val Arg Cys Arg
    450                 455                 460

His Arg Arg Arg Gln Ala Glu Arg Met Ser Gln Ile Lys Arg Leu Leu
465                 470                 475                 480

Ser Glu Lys Lys Thr Cys Gln Cys Pro His Arg Phe Gln Lys Thr Cys
                485                 490                 495

Ser Pro Ile

<210> SEQ ID NO 8
<211> LENGTH: 34
<212> TYPE: PRT
<213> ORGANISM: Human immunodeficiency virus 1

<400> SEQUENCE: 8

Trp Met Glu Trp Asp Arg Glu Ile Asn Asn Ala Thr Ser Leu Ile His
1               5                   10                  15

Ser Leu Ile Glu Glu Ala Gln Asn Gln Gln Glu Lys Asn Glu Gln Glu
            20                  25                  30

Leu Leu

<210> SEQ ID NO 9
<211> LENGTH: 34
<212> TYPE: PRT
<213> ORGANISM: Human immunodeficiency virus 1

<400> SEQUENCE: 9

Ala Met Glu Ala Asp Arg Glu Ala Asn Asn Ala Thr Ser Leu Ala His
1               5                   10                  15

Ser Ala Ile Glu Glu Ala Gln Asn Ala Gln Glu Lys Ala Glu Gln Ala
            20                  25                  30

Leu Leu

<210> SEQ ID NO 10
<211> LENGTH: 49
<212> TYPE: DNA
<213> ORGANISM: Homo sapiens

<400> SEQUENCE: 10
```

```
gatatacact tcagataact acaccgagga aatgggctca ggggactat        49
```

<210> SEQ ID NO 11
<211> LENGTH: 28
<212> TYPE: DNA
<213> ORGANISM: Homo sapiens

<400> SEQUENCE: 11

```
aggaaatggg ctcaggggac tatgactc                                28
```

<210> SEQ ID NO 12
<211> LENGTH: 28
<212> TYPE: DNA
<213> ORGANISM: Homo sapiens

<400> SEQUENCE: 12

```
gtgtagttat ctgaagtgta tatctgca                                28
```

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ser Asp His Leu Ser Asn
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ser His Asp Arg Thr Lys
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Arg Ser His Leu Ala Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Asp Ser Leu Ser Ala
1               5

```
<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Ser Gly Asn Leu Ala Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ser Asp Ala Leu Ala Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Ala Tyr Asp Arg Arg Lys
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Ser Gly Ser Leu Ser Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Ser Gly Ser Leu Thr Arg
1               5

<210> SEQ ID NO 22
<211> LENGTH: 9
<212> TYPE: PRT
<213> ORGANISM: Unknown
<220> FEATURE:
<223> OTHER INFORMATION: Description of Unknown: "LAGLIDADG"
      family peptide
```

```
<400> SEQUENCE: 22

Leu Ala Gly Leu Ile Asp Ala Asp Gly
1               5
```

METHODS AND COMPOSITIONS FOR INHIBITING VIRAL ENTRY INTO CELLS

CROSS-REFERENCE TO RELATED APPLICATIONS

The present application claims the benefit of U.S. Provisional Application No. 61/404,063, filed Sep. 27, 2010, the disclosure of which is hereby incorporated by reference in its entirety.

STATEMENT OF RIGHTS TO INVENTIONS MADE UNDER FEDERALLY SPONSORED RESEARCH

Not applicable.

TECHNICAL FIELD

The present disclosure is in the fields of gene modification and inhibition of viral entry into cells, including anti-HIV therapies.

BACKGROUND

Human immunodeficiency virus (HIV)-1 is the causative agent of acquired immunodeficiency syndrome (AIDS). HIV-1 entry into target cells is initiated by a high-affinity binding of HIV-1 envelope gp120 glycoprotein to the primary receptor CD4, and the subsequent interaction of CD4-bound gp120 with the appropriate chemokine receptor (co-receptor), either CXCR4 or CCR5. See, e.g., Feng et al. (1996) *Science* 272:872-877; Deng et al. (1996) *Nature* 381:661-666. Most HIV strains are dependent upon the CD4/CCR5 receptor/co-receptor combination to gain entry into a cell and are termed CCR5 (or R5) tropic. Some viral strains however are dependent on the CD4/CXCR4 receptor/co-receptor combination and are termed CXCR4 (or X4) tropic, while others can utilize both the CD4/CCR5 and CD4/CXCR4 combinations and are termed dual (or R5/X4) tropic.

The engagement of gp120 with the correct co-receptor leads to the exposure of the viral gp41 fusion peptide (FP), which inserts into the target cell membrane producing a so-called pre-hairpin intermediate bridging the viral and host cell membranes. In the pre-hairpin structure, the N-terminal heptad repeat (NHR) of gp41 forms a trimeric coiled-coil, onto which the C-terminal heptad repeat (CHR) of gp41 folds to form a 6-helical bundle (also called trimer-of-hairpins). The formation of trimer-of-hairpins drives the two membranes in close apposition, and ultimately leads to membrane fusion and the release of the viral nucleocapsid core into the cells. See, e.g., Chan et al. (1997) *Cell* 89:263-273; Eckert et al. (2001) *Annu Rev Biochem* 70:777-810.

The pre-hairpin intermediate has a relatively long half-life (see, e.g., Munoz-Barroso et al. (1998) *J Cell Biol* 140:315-323) and constitutes a target for active new drug development. Several peptides derived from the NHR and CHR regions of gp41, designated N- and C-peptides, respectively, have potent anti-HIV fusion activity, through blocking the formation of trimer-of-hairpins or other mechanisms. Examples of such anti-HIV fusion C-peptides are SJ-2176, T-20, N36 and C34. (Liu et al. (2005) *J Biol Chem* 280: 11259-11273). Such peptide fusion inhibitors can potentially become anti-HIV therapeutics. For example, fuzeon (also known as T-20 or enfuvirtide), one of the synthetic C-peptides, was the first peptide fusion inhibitor to gained Food and Drug Administration (FDA) approval for use to treat AIDS (Rockstroh et al. (2004) *Antimicrob Chemother* 53:700-702).

At least some peptide fusion inhibitors appear to tolerate being used in protein conjugation or membrane-anchoring. For example, an albumin-conjugated C34 peptide fusion inhibitor exhibited improved anti-HIV activity in vivo (Stoddart et al. (2008) *J Biol Chem* 283:34045-34052). Other examples include a membrane-anchored N-peptide made by conjugating with a fatty acid (Wexler-Cohen et al. (2009) *PLoS Pathog* 5, e1000509) and a C-peptide made by addition of a cholesterol group (Ingallinella et al. (2009) *Proc Nat'l Acad Sci USA* 106:5801-5806), which also exhibited improved anti-HIV activity. Furthermore, direct membrane-anchored (surface expressed) peptide fusion inhibitor exhibited potent anti-HIV activities in vitro (see, e.g., Hildinger et al. (2001) *J Virol* 75(6):3038-42 and Egelhofer et al. (2004) *J Virol* 78(2):568-75), and importantly, conferred a survival advantage to cells expressing a peptide fusion inhibitor both in vitro and in vivo in the presence of simian immunodeficiency virus (SIV) or HIV (see, e.g., Kimpel et al. (2010) *PLoS One* 5(8); Zahn et al. (2008) *Gene Ther* 15(17):1210-22).

Entry of HIV-1 into target cells can be prevented by targeted disruption or knock-out of the HIV-1 coreceptors. U.S. Patent Publication Nos. 20080159996 and 20100291048 disclose nuclease-mediated genomic modification of CCR5 and CXCR4. However, the disruption or knock-out of viral receptors such as CXCR4 may have undesired consequences in some circumstances, for example, a hampered response to its natural chemokine ligand, CXCL12, which is involved in T cell homing and inflammatory responses.

Thus, there remains a need for the development of novel anti-HIV strategies to prevent HIV infection without disruption of the normal chemokine receptor functions, for instance by developing methods and compositions for attachment of a peptide fusion inhibitor to a cell surface (e.g., viral) receptor to inhibit viral entry and treat viral diseases.

SUMMARY

Disclosed herein are methods and compositions for inhibiting or preventing viral entry into a cell by fusing or attaching a peptide fusion inhibitor to an HIV receptor or co-receptor (e.g., CD4, CCR5, CXCR4, etc.) to block the HIV entry process. In particular, the methods involve integrating, using one or more nucleases, a sequence encoding a peptide fusion inhibitor such that it is expressed as part of a fusion protein composed of the peptide fusion inhibitor and a cell surface receptor involved in viral entry. In the presence of the peptide fusion inhibitor expressed with the cell surface receptor, viral entry into the cell via the cell surface receptor is inhibited. The genetic modification of an HIV receptor or co-receptor can also be achieved in two steps, i.e., disruption/knock-out of the HIV receptor or coreceptor gene using nucleases first, followed by delivery of constructs (e.g., viral or non-viral vectors) encoding the above mentioned peptide fusion inhibitor:cell surface receptor fusion protein into the cells, at the disrupted locus and/or a different locus.

Thus, in one aspect, provided herein is a cell comprising an exogenous sequence encoding a peptide fusion inhibitor, wherein the exogenous sequence is integrated into the genome of the cell using one or more nucleases such that the peptide fusion inhibitor is expressed as a fusion protein with a viral receptor or viral co-receptor. In certain embodiments, the sequence is integrated into an endogenous locus encoding a viral receptor or a viral co-receptor such that the peptide fusion inhibitor is expressed with the viral receptor or co-receptor (e.g., the peptide fusion inhibitor is integrated into the genome such that it is expressed at the N-terminus of the viral receptor or co-receptor). In any of the embodiments described herein, the sequence can further encode a viral receptor or co-receptor such that the peptide fusion inhibitor is expressed as a fusion protein with a viral receptor or co-receptor (e.g., at the N-terminus) of the exogenous sequence. In certain embodiments, when the sequence encodes a peptide fusion inhibitor and viral receptor or co-receptor, the sequence is inserted in a safe harbor locus, into an endogenous viral receptor or co-receptor gene (e.g., so that the endogenous gene is inactivated) and/or may be randomly integrated into the genome of the cell. In any of the cells described herein, the peptide fusion inhibitor may comprise any natural or synthetic N- or C-peptide, for example, C34 or fuzeon. Similarly, the viral receptor or receptor may comprise an HIV receptor (e.g., CD4) or co-receptor (e.g., CCR5, CXCR4, etc.).

In another aspect, the invention encompasses modified cells wherein cells contain one or more viral receptors that are disrupted by specific nucleases, and are further modified by inclusion of a peptide fusion inhibitor (e.g., C34-receptor fusion). In some aspects, cells in which the wild-type CCR5 gene is disrupted by CCR5-specific nucleases are then further modified by the insertion of the nucleic acid encoding the C34 fusion peptide in frame in the wild-type CXCR4 locus so that a C34-CXCR4 fusion protein will be encoded. In other embodiments, the C34-CXCR4 encoding nucleic acid sequence is integrated into the wild-type CXCR4 locus so that the wild-type CXCR4 locus is disrupted for wild-type CXCR4 expression at the same time. In some aspects, at least one peptide fusion inhibitor construct (e.g., C34, C34-CXCR4, C34-CCR5, and/or or C34-CD4) is specifically integrated into a CXCR4, a CCR5, and/or a CD4 locus to both disrupt the wild-type gene and integrate the peptide fusion inhibitor at the same time. In any of the aspects described above, the nuclease(s) may be one or more viral-receptor specific zinc finger nucleases, TALENs and/or homing endonucleases.

In another aspect, provided herein are methods for preventing or reducing viral (e.g., HIV) infection. In certain embodiments, a cell as described herein (e.g., expressing a viral (e.g., HIV) receptor or co-receptor and peptide fusion inhibitor) is introduced into a subject, thereby inhibiting or preventing viral infection in the cell. In any of the methods described herein, one or more nucleases are used to integrate a sequence encoding a peptide fusion inhibitor (e.g., natural or synthetic N- or C-peptide such as C34, or fuzeon) to a viral receptor (e.g. CD4) or co-receptor (e.g., CCR5, CXCR4, etc.) in the genome of the cell such that the peptide fusion inhibitor and viral receptor or co-receptor encoded by the sequence is expressed, thereby preventing or inhibiting viral infection. In certain embodiments, the peptide fusion inhibitor is integrated at the N-terminus of the viral receptor or co-receptor. In certain embodiments, the methods of inhibiting viral entry result in treatment of or prevention of viral diseases, for example the treatment or prevention of HIV infection/AIDS. Alternatively, constructs (e.g., viral or non-viral vectors) encoding the fusion protein comprising the peptide fusion inhibitor and the viral receptor or co-receptor is delivered into cells, which have previously been modified using nucleases (see, e.g., U.S. Patent Publication Nos. 20080159996 and 20100291048 which disclose nuclease-mediated genomic modification of CCR5 and CXCR4). In some aspects, the nucleic acid construct encoding the fusion protein is inserted into the wild-type receptor locus. In other aspects, the construct is inserted in a "safe harbor" locus such as AAVS1 (see co-owned United States Patent Publication 20080299580). In some aspects, the construct is inserted into the genome through random integration.

In any of the compositions (e.g., cells) or methods described herein, the peptide fusion inhibitor sequence can be integrated into the surface protein (e.g., cell surface receptor) using a viral vector, a non-viral vector (e.g., plasmid) and/or combinations thereof. In certain embodiments, the vector comprises an AAV vector, such as AAV8.

In any of the methods described herein, the nuclease can be one or more zinc finger nucleases (ZFN), one or more homing endonucleases (meganucleases) and/or one or more TAL-effector domain nucleases ("TALEN").

The methods described herein can be practiced in vitro, ex vivo or in vivo. In certain embodiments, the compositions are introduced into a live, intact mammal. The mammal may be at any stage of development at the time of delivery, e.g., embryonic, fetal, infantile, juvenile or adult. Additionally, the animals may be healthy or diseased. In certain embodiments, the compositions (e.g., polynucleotides encoding nuclease(s) and/or peptide fusion inhibitor-encoding sequences) are delivered to ex vivo, for example to cells (e.g., stem cells) isolated from the subject animal, which may then be returned to the animal.

The target cells may be human cells, or cells of other mammals, especially nonhuman primates and mammals of the orders *Rodenta* (mice, rats, hamsters), *Lagomorpha* (rabbits), *Carnivora* (cats, dogs), and *Arteriodactyla* (cows, pigs, sheep, goats, horses). Furthermore, the cell may be, for example, a stem cell (e.g., hematopoietic stem cell such as a CD34+ cell), a T-cell (e.g., a CD4+ cell), a monocyte, a macrophage, a microglia cell, a dendritic cell and/or an antigen-presenting cell.

These and other aspects will be readily apparent to the skilled artisan in light of disclosure as a whole.

BRIEF DESCRIPTION OF THE DRAWINGS

FIG. 2, panels A and B, are models of HIV membrane fusion. FIG. 2A shows a model of HIV membrane fusion. The HIV envelope glycoprotein is organized as trimers on the membrane of the virus, and is composed of two non-covalently associated subunits, gp120 and gp41 (proteolytic products of gp160). HIV-1 entry into target cells is initiated by a high-affinity interaction between HIV-1 gp120 and the primary receptor CD4, which induces conformation change in gp120. The subsequent interaction of CD4-bound gp 120 with the appropriate chemokine receptor (co-receptor), either CXCR4 or CCR5, leads to the exposure of the gp41 fusion peptide (FP), which inserts into the target cell membrane producing a so-called pre-hairpin intermediate bridging the viral and host cell membranes. In the prehairpin structure, the NHR of gp41 forms a trimeric coiled-coil, onto which the CHR of gp41 folds to form a 6-helical bundle (also called trimer-of-hairpins), the formation of which drives the two membranes in close apposition, ultimately leading to their fusion and the release of the viral nucleocapsid core into the cells. FIG. 2B shows an exemplary embodiment of the present invention in which the C34-peptide derived from the CHR of gp41 is fused to the N-terminus of CXCR4 to block entry of the virus into the cell. During the fusion process, the C34 peptide is able to bind to the pocket binding grooves formed between the two NHRs of the pre-hairpin intermediate. To simplify the illustration, only single CD4 and C34-CXCR4 molecules are shown instead of three of each. The C34 binding therefore prevents the folding of gp41CHR to form the stable structure of trimer-of-hairpins and eventually abolishes the fusion process.

FIG. 3 shows partial genotypes of the wild-type CXCR4 allele (SEQ ID NO:1) and CXCR4 alleles B4-seq 1 (SEQ ID NO:2) and B4-seq 2 (SEQ ID NO:3) of the CXCR4−/− B4 SupT1 cell line at their native loci. CXCR4−/− B4 had been previously modified at the CXCR4 locus using ZFN-mediated gene editing. Sections of the CXCR4 gene containing DNA sequence of the primary binding site for CXCR4-targeted ZFNs (see, U.S. Patent Publication No. 20100291048) are underlined. A "−" indicates a deletion and demonstrates the two alleles of the CXCR4−/− B4 strain whose CXCR4 deletions render the CXCR4 receptor non-functional. This cell line was then used for the random integration of either a C34-CXCR4 encoding nucleic acid construct or a wild-type CXCR4 gene.

FIG. 4A shows migration of wild-type ("wt" circles) and CXCR4$^{-/-}$ B4 SupT1 cells (squares). FIG. 4B shows migration of transduced B4 SupT1 cells in which genes encoding GFP (diamonds) or the C34-CXCR4 fusion protein (squares) were randomly integrated into the genome using a lentiviral vector delivery system.

FIG. 6 depicts alignment of sequences of the C34 peptide (SEQ ID NO:5) with sequences of two C34 mutants. In the C34S2 peptide (SEQ ID NO:8), two amino acids (underlined) have been altered (Y638A, S649A), while in the C34S10 peptide (SEQ ID NO:9), ten amino acids (underlined) have been altered (W628A, W631A, I635A, Y638A, I642A, L645A, S649A, Q652A, N656A, E659A).

FIG. 7A depicts the results of supplying wild type CCR5 co-receptor or C34-CCR5 fusion co-receptor or a 1:1 mixture of the two thereof in the presence of a CCR5-tropic HIV strain YU2. FIG. 7B depicts the results using a CCR5/CXCR4 dual tropic HIV strain R3A in the presence of C34-CCR5 co-receptor, or when C34 is fused to the CD4 receptor (indicated by *, C34-CD4 is supplied instead of CD4). Viral entry into the cells occurs when the wild type homologous co-receptor is supplied but not when the co-receptor is fused to C34. In addition, fusion of the C34 to CD4 does not inhibit viral entry in this experiment (see FIG. 7B).

FIG. 8A depicts activity for the CXCR4 tropic HIV strain HxB where the CXCR4 co-receptor was supplied either as a wild type sequence or as a fusion with either wild type C34, or the S2 or S10 C34 mutants. The HxB virus was only able to enter cells containing the wild type CXCR4 co-receptor or the S10 C34-CXCR4 fusion. Similar results were seen in FIG. 8B, where the CXCR4 tropic strain BK132 was only able to enter the cells expressing either wild type CXCR4 or the S10 C34-CXCR4 fusion protein. FIG. 8C depicts the results for the CCR5/CXCR4 dual tropic HIV strain R3A where the virus was able to enter the cell when the wild type CXCR4 co-receptor or the S10 C34 CXCR4 fusions were supplied, or when the wild type CXCR4 receptor was supplied in the presence of the C34-CD4 HIV receptor fusion in place of the wild type CD4 (indicated by *). The S10 C34 mutant lost the viral inhibition activity of the C34 peptide.

FIGS. 9A and 9B depicts the activity using the dual tropic R3A HIV strain. FIG. 9C shows the activity using the CXCR4 tropic virus HxB and FIG. 9D depicts the results using the CCR5 tropic strain YU2. In all cases, the virus strains were able to enter the cells in the presence of a wild type copy of the co-receptor utilized by the strain, while in the presence of the C34 fused co-receptor only, no entry was observable. When the cells were transfected with a mixture of the wild type and C34 fused co-receptors, as the percent of wild type co-receptor expression plasmid increased, the amount of viral entry similarly increased. In all cases, the CD4 receptor was supplied on an expression plasmid co-transfected into the cells.

FIG. 10A depicts the results using the CCR5/CXCR4 dual tropic HIV strain R3A where the presence of C34 fused to either the CXCR4 or CCR5 co-receptor was able to inhibit viral entry. FIG. 10B depicts the results using the CCR5 tropic virus YU2. C34 fused to either the CCR5 or the CXCR4 co-receptor was able to inhibit viral entry although this strain is only dependent on the CCR5 co-receptor. In all cases, the CD4 receptor was also supplied on an expression plasmid co-transfected into the cells.

DETAILED DESCRIPTION

Figure 1:
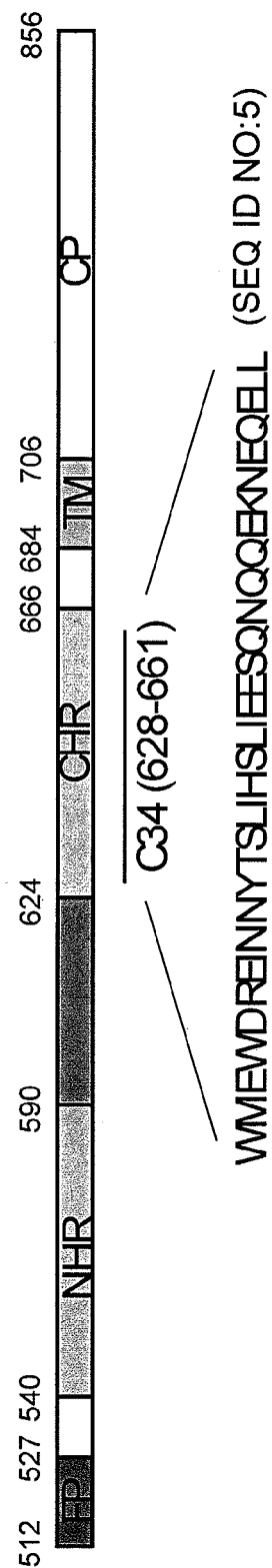
FIG. 1 is a schematic depicting the HIV-1 gp41 protein. The residue number corresponds to its position in HIV-1 HXB gp160. "FP" refers to a fusion peptide; "NHR" refers to the N-terminal heptad repeat; "CHR" refers to the C-terminal heptad repeat; "TM" refers to the transmembrane domain; and "CP" refers to the cytoplasmic domain. "C34" depicts the region of the CHR from which the C34 peptide is derived and displays its sequence (SEQ ID NO:5).

Disclosed herein are compositions and methods for treating and/or preventing viral (e.g., HIV) entry into a cell, thereby treating and/or preventing viral infection and resulting disease (e.g., HIV/AIDS). In particular, nuclease-mediated integration is used to integrate a peptide fusion inhibitor onto a cell surface receptor involved in viral entry. Alternatively, the HIV receptor or coreceptor gene is disrupted using nucleases, and the constructs (e.g., viral or non-viral vectors) encoding the fusion protein comprising the peptide fusion inhibitor and the viral receptor or coreceptor is delivered into the modified cells (at the disrupted locus or a different locus). In other aspects, one or more of the viral receptors are disrupted by specific nucleases and then the fusion construct is delivered to inhibit viral entry.

In certain aspects, the virus is HIV and the peptide fusion inhibitor is integrated onto the N-terminus of an HIV receptor or coreceptor (e.g., CD4, CCR5, or CXCR4). In certain embodiments, the HIV coreceptor is a CXCR4 receptor. Attachment of a peptide fusion inhibitor (e.g., C34) onto the N-terminus of CXCR4 renders the modified cells resistant to HIV infection by blocking the formation of a trimer-of-hairpins while retaining the response to CXCL12.

The compositions and methods described herein can be used for therapies for treating viral diseases, such as anti-HIV/AIDS therapies, by inhibiting entry of the virus. In addition, compositions and methods described herein can be used for any research studies or other applications involving HIV receptor/co-receptor proteins or other surface proteins, such as studying functions of the protein under physiological or pathological conditions.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084 and U.S. Publication No. 20110301073.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms.

This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of nuclease proteins (e.g., ZFNs and/or TALENs) can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528 and 2008/0131962, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and one or more activation domains or an anti-HIV fusion peptide and an HIV co-receptor) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to an activation domain, the ZFP DNA-binding domain and the activation domain are in operative linkage if, in the fusion polypeptide, the ZFP DNA-binding domain portion is able to bind its target site and/or its binding site, while the activation domain is able to up-regulate gene expression. When a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

Nucleases

Described herein are compositions, particularly nucleases, which are useful in integration of a peptide fusion inhibitor into a cell surface receptor (e.g., viral receptor) or disruption of the cell surface receptor to inhibit entry of macromolecules that bind to the cell surface receptor. In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains).

A. DNA-Binding Domains

In certain embodiments, the nuclease is a meganuclease (homing endonuclease). Naturally-occurring meganucleases recognize 15-40 base-pair cleavage sites and are commonly grouped into four families: the LAGLIDADG (SEQ ID NO: 22) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

In certain embodiments, the nuclease comprises an engineered (non-naturally occurring) homing endonuclease (meganuclease). The recognition sequences of homing endonucleases and meganucleases such as I-SceI, I-CeuI, PI-PspI, PI-SceI, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J Mol. Biol.* 263:163-180; Argast et al. (1998) *J Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain comprises a naturally occurring or engineered (non-naturally occurring) TAL effector DNA binding domain. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. See, e.g., U.S. Publication No. 20110301073. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the code for DNA recognition of these TAL-effectors has been determined such that an HD sequence at positions 12 and 13 leads to a binding to cytosine (C), NG binds to T, NI to A, C, G or T, NN binds to A or G, and IG binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target). Christian et al ((2010)<*Genetics* epub 10.1534/genetics. 110.120717). See, also, U.S. Publication No. 20110301073.

In certain embodiments, the DNA binding domain comprises a zinc finger protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534, 261; 6,599,692; 6,503,717; 6,689,558; 7,030,215; 6,794, 136; 7,067,317; 7,262,054; 7,070,934; 7,361,635; 7,253, 273; and U.S. Patent Publication Nos. 2005/0064474; 2007/ 0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, DNA domains (e.g., multi-fingered zinc finger proteins) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The zinc finger proteins described herein may include any combination of suitable linkers between the individual zinc fingers of the protein. In addition, enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Nat'l Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014275.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. Patent Publication No. 20110201055).

Engineered cleavage half-domains described herein can be prepared using any suitable method, for example, by site-directed mutagenesis of wild-type cleavage half-domains (Fok I) as described in U.S. Patent Publication Nos. 20050064474; 20080131962 and 20110201055).

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

Target Sites

As described in detail above, DNA domains can be engineered to bind to any sequence of choice. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Publication No. 20110301073.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Publication No. 20110301073.

For anti-HIV therapies, a peptide fusion inhibitor can be integrated (via nucleases) into any cell surface protein. DNA-binding domains of the nucleases may be targeted to any desired site in the genome. The sequence encoding the peptide fusion inhibitor can be integrated anywhere in cell surface gene, for example at the C-terminal or N-terminal end. Multiple copies may be integrated at the same or different locations. In certain embodiments, the peptide fusion inhibitor is integrated into a locus encoding an HIV receptor or co-receptor (e.g., CXCR4, CCR5, etc.). Non-limiting examples of other cell surface proteins include additional HIV coreceptors such as CCR2b, CCR3, CCR8, CX3CR1/GPR13, CXCR6/CD186/Bonzo/STRL33, CXCR7/RDC1, D6/CCBP2, GPR1, GPR15 (Gabuzda and Wang (2000) *J Neurovirol* 6 Suppl 1: S24-43), (Lusso (2006), *EMBO J.* 25(3):447-456).

Peptide Fusion Inhibitors

For inhibition of virus entry into a cell mediated by a cell surface receptor, the integrated (donor) sequence encodes any functional peptide fusion inhibitor. The peptide fusion inhibitor integrated into cell surface receptor gene can be naturally occurring, a portion of a naturally occurring peptide or synthetic. Non-limiting examples of suitable peptide fusion inhibitions include C-HR based peptides (such as C34, C34M3, C42, C43, CP32M, CP621-652, DP, DP-C8-C16, SC34EK, SC29EK, sifuvirtide, T-20, T649, T1249, T2544, and T2635) and N-HR based peptides (such as N36, T21, N42, N36F10, and IZN17) See, e.g., Naider and Anglister (2009), *Curr Opin Struct Biol* 19(4):473-482, Naito et al. (2009) *Antimicrobial Agents and Chemotherapy* 53(3):1013-1018; Gupta et al. (2006) *Retrovirology* 2006; 3(Suppl 1):S86; Munoz-Barroso et al. (1998) *J Cell Biol* 140:315-323; Rockstroh et al. (2004) *J Antimicrob Chemother* 53:700-702; Liu et at (2005) *J Biol Chem*

280:11259-11273; Wexler-Cohen et al. (2009) *PLoS Pathog* 5, e1000509; Stoddart et al. (2008) *J Biol Chem* 283:34045-34052.

As noted above, in some embodiments, the sequence encoding the peptide fusion inhibitor is integrated into the genome of the cell such that it is expressed with a viral receptor or co-receptor (e.g., at the N-terminus of the viral receptor or co-receptor) as a fusion protein. In other embodiments, the sequence integrated into the genome encodes a fusion protein comprising the peptide fusion inhibitor and a viral receptor or co-receptor.

The peptide fusion inhibitor donor sequence can be introduced into the cell prior to, concurrently with, or subsequent to, expression of the nucleases(s). The donor polynucleotide carrying the peptide fusion inhibitor typically contains sufficient homology to a genomic sequence to support homologous recombination (or homology-directed repair) between it and the genomic sequence to which it bears homology. See, e.g., U.S. Patent Publication Nos. 2005/0064474; 2007/0134796 and 2009/0263900.

It will be readily apparent that the donor sequence is typically not identical to the genomic sequence that it replaces. For example, the sequence of the donor polynucleotide can contain one or more single base changes, insertions, deletions, inversions or rearrangements with respect to the genomic sequence, so long as sufficient homology with chromosomal sequences is present. Alternatively, a donor sequence can contain a non-homologous sequence flanked by two regions of homology. Alternatively, a donor sequence can be a non-homologous sequence that is integrated by end capture during non-homologous end joining (NHEJ) driven by the introduction of a double strand break by an engineered nuclease. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the cell surface receptor with which the peptide fusion inhibitor is expressed. However, it will be apparent that the donor may comprise a promoter and/or enhancer, for example a constitutive promoter or an inducible or tissue specific promoter that drives expression of the function peptide fusion inhibitor upon integration.

Furthermore, although not required for expression, exogenous sequences may also be transcriptional or translational regulatory sequences, for example, promoters, enhancers, insulators, internal ribosome entry sites, sequences encoding 2A peptides and/or polyadenylation signals.

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the DNA binding protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids (e.g., nucleic acids encoding engineered nucleases or for donor molecules) take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al. *J. Virol.* 66:1635-1640 (1992); Sommerfelt et al. *Virol.* 176:58-59 (1990); Wilson et al. *J. Virol.* 63:2374-2378 (1989); Miller et al., *J Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV7, AAV8, AAV9 and AAVrh.10 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al.,

*Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and $\psi 2$ cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (nuclease-encoding and/or peptide fusion inhibitor-encoding) described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; WO 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, a donor polynucleotide can be carried by a plasmid, while the one or more nucleases can be carried by a AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Thus, the instant disclosure includes in vivo or ex vivo treatment of viral diseases, via nuclease-mediated integration of peptide fusion inhibitor-encoding sequence. The sequence encoding the peptide fusion inhibitor is integrated so as to be expressed with a cell surface protein that mediates virus entry into the cell. Expression of the peptide fusion inhibitor with the cell surface protein blocks viral entry into the cell.

The compositions are administered to a human patient in an amount effective to obtain the desired expression of the peptide fusion inhibitor with the cell surface receptor. Administration can be by any means in which the polynucleotides are delivered to the desired target cells. For example, both in vivo and ex vivo methods are contemplated. In vivo administration modes include, for example, injection (intravenously or intraperitoneally) or mucosal administration. Ex vivo modes of administration include transduction in vitro of any cell, for example, an induced pluripotent stem cell (iPSC), an embryonic stem cell, a hematopoietic stem/progenitor cell (e.g., $CD34^+$ cells), a T-cell (e.g., $CD4^+$ T-cell), a macrophage, a dendritic cell and an antigen-presenting cell, peripheral Blood Mononuclear Cells (PBMCs), microglia cells, monocytes, mesenchymal stem cells, or antigen-presenting cells; or a cell line such as K562 (chronic myelogenous leukemia), HEK293 (embryonic kidney), PM-1 ($CD4^+$ T-cell), Sup-T1 (lymphoblastic leukemia), THP-1 (monocytic leukemia) or GHOST (osteosarcoma) cells.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

The following Examples relate to exemplary embodiments of the present disclosure in which the nuclease comprises a zinc finger nuclease (ZFN). It will be appreciated that this is for purposes of exemplification only and that other nucleases can be used, for instance homing endonucleases (meganucleases) with engineered DNA-binding domains and/or fusions of naturally occurring or engineered homing endonucleases (meganucleases) DNA-binding domains and heterologous cleavage domains or TALENs.

EXAMPLES

Example 1

Disruption of Endogenous CXCR4 Gene and Reconstitution with a Sequence Encoding a Fusion Protein Composed of the Peptide Fusion Inhibitor C34 and CXCR4

Endogenous CXCR4 gene was disrupted by ZFN-mediated genome editing, followed by re-introduction of a sequence encoding a fusion protein composed of C34 and CXCR4 (C34-CXCR4 or more specifically, C34-X4b as the predominantly transcribed/expressed form, isoform b of CXCR4 was used in these studies) to render the modified cells resistant to HIV infection but responsive to CXCL12 signaling through random integration of the gene encoding the C34-CXCR4 fusion. In particular, the CXCR4$^{-/-}$ SupT1 B4 cell line described in U.S. Patent Publication No. 20100291048 was used as the parental cell line to generate a C34-CXCR4 transfectant. One CXCR4 allele of the parental B4 SupT1 has a 12 bp deletion, the other CXCR4 allele has a 19 bp deletion in exon 2 (FIG. 3A).

The parental CXCR4$^{-/-}$ B4 SupT1 cells were transduced with lentiviral constructs encoding either GFP, wild-type CXCR4 isoform B (X4b-WT), or C34-CXCR4 isoform B (C34-X4b) to generate stable cell lines. The amino acid sequence of C34-X4b is as follows, with the C34 sequence shown in straight underlining (SEQ ID NO:5) and the CXCR4 isoform B shown in bold with wavy underlining:

(SEQ ID NO: 4)
MWMEWDREINNYTSLIHSLIEESQNQQEKNEQELLLKTMEGISIYTSDNY

TEEMGSGDYDSMKEPCFREENANFNKIFLPTIYSIIFLTGIVGNGLVILV

MGYQKKLRSMTDKYRLHLSVADLLFVITLPFWAVDAVANWYFGNFLCKAV

HVIYTVNLYSSVLILAFISLDRYLAIVHATNSQRPRKLLAEKVVYVGVWI

PALLLTIPDFIFANVSEADDRYICDRFYPNDLWVVVFQFQHIMVGLILPG

IVILSCYCIIISKLSHSKGHQKRKALKTTVILILAFFACWLPYYIGISID

SFILLEIIKQGCEFENTVHKWISITEALAFFHCCLNPILYAFLGAKFKTS

AQHALTSVSRGSSLKILSKGKRGGHSSVSTESESSSFHSS

Surface expression of CXCR4 on the parental CXCR4$^{-/-}$ B4 SupT1 cells, and X4b-WT or C34-X4b transfectant was evaluated by flow cytometry analysis. Briefly, B4 SupT1 transfectants were incubated with isotype controls (mIgG1 and mIgG2a) or the anti-CXCR4 monoclonal antibodies 4G10 (Santa Cruz Biotechnology, Inc.), or 12G5 (BD Biosciences), washed, then incubated with PE-conjugated goat anti-mIgG. Cells were then washed again and analyzed with a Guava flow cytometer (Millipore). Results of the frequency (%) of positively stained cells and mean fluorescence intensity (MFI) of the antibody staining is shown in Table 1.

TABLE 1

Surface CXCR4 expression on B4 SupT1 transfectants

|  | mIgG1 (%) | 4G10 (%) | 4G10 (MFI) | mIgG2a (%) | 12G5 (%) | 12G5 (MFI) |
|---|---|---|---|---|---|---|
| Parent | 0.08 | 1.9 | 21.08 | 0.46 | 0.24 | 4.09 |
| X4b WT | 0 | 96.07 | 494.91 | 0.98 | 95.84 | 214.48 |
| C34-X4b | 0 | 90.62 | 336.52 | 0.39 | 96.59 | 253.39 |

Thus, the C34-X4b and X4b-WT transfectants have comparable levels of CXCR4 expression on their surface based on surface staining with 4G10 and 12G5 monoclonal antibodies, which recognize the N-terminus and the second extracellular loop of CXCR4, respectively.

Alternatively, the C34-CXCR4 fusion is made by targeted integration of a C34 into a endogenous CXCR4 gene to produce the C34-CXCR4 fusion. In one approach, C34 is introduced at the N-terminus of the endogenous CXCR4 gene such that the expression of the C34-CXCR4 fusion is controlled by the endogenous CXCR4 promoter. ZFNs 28945 and 28947 are made to target the sequence (SEQ ID NO:10) shown below corresponding to the sequences encoding the N-terminus of the CXCR4 protein:

```
5'-                                         28947
GATATACACTTCAGATAACTACACCGAGGAAATGGGCTCAGGGGACTAT
                                             -3'

3'-
CTATATGTGAAGTCTATTGATGTGGCTCCTTTACCCGAGTCCCCTGATA
      28945                                  -5'
```

The characteristics of the CXCR4 specific ZFNs are shown below in Table 2 which displays the recognition helices for each of the fingers in the DNA binding domains and the target sites for the ZFNs.

TABLE 2

CXCR4-specific ZFNs

| ZFN Name target | F1 | F2 | F3 | F4 | F5 |
|---|---|---|---|---|---|
| ZFN 28947 agGAAATGG GCTCAGGGg actatgactc (SEQ ID NO: 11) | RSDHLSN (SEQ ID NO: 13) | QSHDRTK (SEQ ID NO: 14) | DRSHLAR (SEQ ID NO: 15) | RSDSLSA (SEQ ID NO: 16) | QSGNLAR (SEQ ID NO: 17) |
| ZFN 28945 gtGTAGTTa TCTGAAGTG tatatctgca (SEQ ID NO: 12) | RSDALAR (SEQ ID NO: 18) | QSGNLAR (SEQ ID NO: 17) | LAYDRRK (SEQ ID NO: 19) | TSGSLSR (SEQ ID NO: 20) | QSGSLTR (SEQ ID NO: 21) |

Donor C34 DNAs are co-transfected into B4 SupT1 cells with homology to the target site in the CXCR4 gene to allow insertion of the C34 encoding sequences at the target sequences corresponding to the N-terminus of CXCR4.

In an alternative approach, ZFNs are used to create a knock out of the endogenous CXCR4 gene and an expression cassette comprising the C34-CXCR4 fusion and a promoter is integrated by insertion of the fusion sequence into the endogenous gene. ZFNs targeting the endogenous CXCR4 gene are used as described in co-owned U.S. Patent Publication No. 20100291048. The C34-CXCR4 expression cassette contains the constitutive EF1α or similar promoter and insertion of the transgene occurs by either end capture driven by non-homologous end joining following ZFN-induced double strand break, or by homology driven repair using a donor containing the transgene flanked by DNA sequences that are nearly identical to sequences flanking the ZFN cleavage site.

Example 2

Functional Response to CXCR4 Ligand

Functional responses of cells to the natural CXCR4 ligand CXCL12 (also called stromal-derived factor-1, SDF-1) were also evaluated using a transendothelial migration assay (Wang et al. (1998) *Leukoc Biol* 64(5):642-649). Briefly, the hybrid endothelial cell line EA.hy926 (ATCC) was cultured in transwell inserts (Corning) with 5 nm pores at 37° C. for 3 days. The indicated SupT1 cell lines were loaded into the washed transwell inserts (upper part of the transwell), whereas SDF-1α was added into lower part of the transwell (outside of the inserts). Cells were allowed to migrate at 37° C. for 4 hours, then centrifuged at 1400 rpm for 5 min, and collect for counting with a Guava flow cytometry. The frequency of migrated cells (% of input) was calculated using the following formula: Frequency of migrated cells (% of input)=(number of migrated cells)/(total number of cells added into the transwell insert)×100%.

Figure 4:
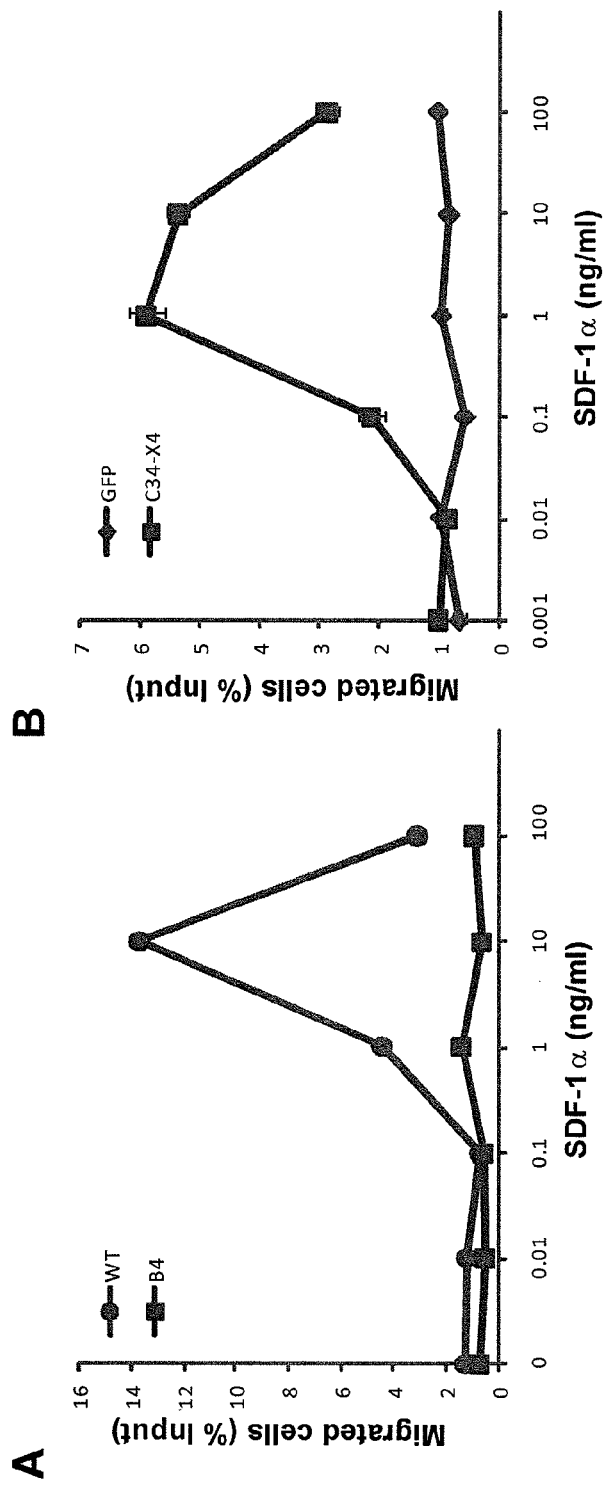
FIG. 4, panels A and B, are graphs depicting migration of SDF-1α-induced transendothelial migration of wild-type and CXCR4-modified B4 SupT1 cells. SDf-1α is the natural ligand for the CXCR4 receptor, and induces transendothelial migration of cells that express a functional CXCR4 receptor.

As shown in FIG. 4, the WT SupT1 cells showed a dose-dependent migration response in the presence of SDF-1α. Significant cell migration was observed in the presence of 1-100 ng/ml of SDF-1α with a peak level at 10 ng/ml. In contrast, the CXCR4−/− B4 SupT1 cell line only showed background level of migration regardless of the doses of SDF-1α, confirming the status of CXCR4 knock-out in this cell line (FIG. 4A). Re-introduction of C34-X4b fusion into the cell line recovered the dose-dependent response to SDF-1α (FIG. 4B). In contrast, the negative control cells, a transfectant expressing GFP that was established in the same way as the C34-X4b fusion transfectant, showed no response to SDF-1α at all (FIG. 4B).

Thus, attachment of the C34 peptide to the N-terminus of CXCR4 has no adverse effect on this normal function of CXCR4, i.e., binding to its natural SDF 1α ligand and transfer of the signal.

Example 3

Resistance to HIV Infection in C34-CXCR4 Containing Cells

Figure 5:
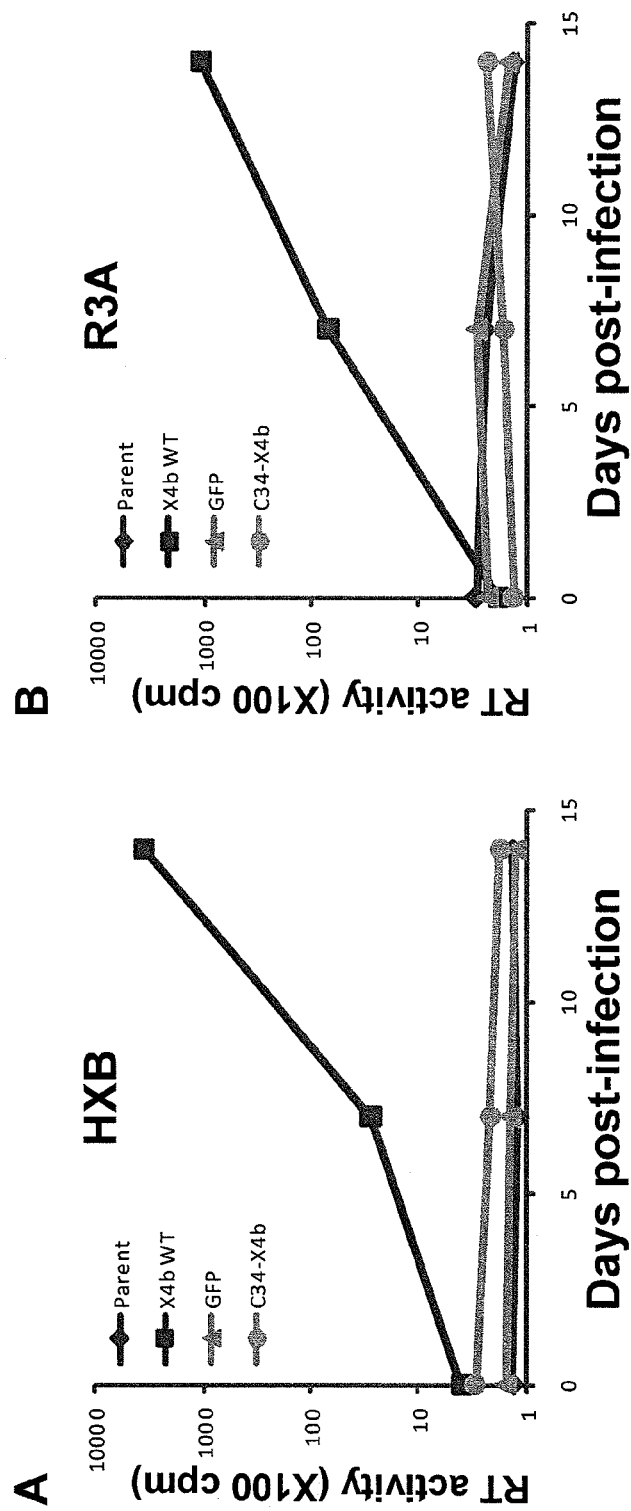
FIG. 5, panels A and B, are graphs depicting HIV encoded reverse transcriptase (RT) activity in the indicated cells following infection with the CXCR4 tropic ("X4") HIV-1 stain HXB (FIG. 5A) or the CCR5/CXCR4 dual tropic ("R5/X4") HIV-1 strain R3A (FIG. 5B). Shown are the results using the CXCR4−/− B4 cell line (parent), the CXCR4−/− B4 line transfected with a wild-type CXCR4 gene (X4bWT), the CXCR4−/− B4 cell line transfected with a GFP gene (GFP) and the CXCR4−/− B4 cell line transfected with the C34-CXCR4 fusion (C34-X4b). Only the X4bWT line is able to support the infection with the HIV strain.

To evaluate whether fusion of the C34 peptide to the N-terminus of CXCR4 co-receptor protein renders cells resistant to HIV-1, the B4 SupT1 transfectants were infected with an X4-tropic HIV-1 strain HXB or a R5/X4 dual-tropic HIV-1 strain R3A and monitored for viral replication by a reverse transcriptase assay. Briefly, cells were plated at 1e6 cells/ml and spin-infected with the indicated HIV-1 strains for 1 hour at 1,500 rpm. Cell culture supernatants were collected over the course of 2 weeks to measure HIV-1 reverse transcriptase (RT) activity As shown in FIG. 5, regardless of the HIV-1 strains used, significant viral replication in the X4b-WT transfectants was detected 7 days post-infection and continued to be about 3 logs higher than background levels 2 week-post-infection. In contrast, no viral replication was detected in the C34-X4b or GFP transfectants as well as the parental B4 SupT1 cells during the experiment. Thus, attachment of C34 to CXCR4 renders cells resistant to R5 tropic and R5/X4 tropic HIV-1 strains under these conditions.

Example 4

Construction of C34-CCR5 and C34-CD4 Fusion Proteins

Similar to the experiment described in Example 1, using standard techniques a construct comprising a gene encoding a fusion of the C34 peptide and the CCR5 protein was generated. The amino acid sequence of C34-CCR5 fusion protein (SEQ ID NO:6) is shown below, with the C34 sequence shown in straight underlining (SEQ ID NO:5) and the CCR5 shown in bold with wavy underlining:

(SEQ ID NO: 6)
MAWMEWDREINNYTSLIHSLIEESQNQQEKNEQELLLKDYQVSSPIYDINYYTSEPCQKI

NVKQIAARLLPPLYSLVFIFGFVGNMLVILILINCKRLKSMTDIYLLNLAISDLFFLLTVPFWAHYAAAQ

WDFGNTMCQLLTGLYFIGFFSGIFFIILLTIDRYLAVVHAVFALKARTVTFGVVTSVITWVVAVFASLPG

IIFTRSQKEGLHYTCSSHFPYSQYQFWKNFQTLKIVILGLVLPLLVMVICYSGILKTLLRCRNEKKRHRA

VRLIFTIMIVYFLFWAPYNIVLLLNTFQEFFGLNNCSSSNRLDQAMQVTETLGMTHCCINPIIYAFVGEK

FRNYLLVFFQKHIAKRFCKCCSIFQQEAPERASSVYTRSTGEQEISVGL

In a similar construction, a construct was produced encoding a fusion protein of the C34 peptide and the CD4 protein. The amino acid sequence of the C34-CD4 fusion protein (SEQ ID NO:7) is shown below, with the C34 sequence shown in straight underlining (SEQ ID NO:5) and the CD4 sequence shown in bold with wavy underlining. In this sequence, the italicized text indicates the CD4 leader sequence:

(SEQ ID NO: 7)
MNRGVPFRHLLLVLQLALLPAATQGKKVVLWMEWDREINN

YTSLIHSLIEESQNQQEKNEQELLEFKKVVLGKKGDTVELTCTASQKKSI

QFHWKNSNQIKILGNQGSFLTKGPSKLNDRADSRRSLWDQGNFPLIIKNL

KIEDSDTYICEVEDQKEEVQLLVFGLTANSDTHLLQGQSLTLTLESPPGS

SPSVQCRSPRGKNIQGGKTLSVSQLELQDSGTWTCTVLQNQKKVEFKIDI

VVLAFQKASSIVYKKEGEQVEFSFPLAFTVEKLTGSGELWWQAERASSSK

SWITFDLKNKEVSVKRVTQDPKLQMGKKLPLHLTLPQALPQYAGSGNLTL

ALEAKTGKLHQEVNLVVMRATQLQKNLTCEVWGPTSPKLMLSLKLENKEA

KVSKREKAVWVLNPEAGMWQCLLSDSGQVLLESNIKVLPTWSTPVQPMAL

IVLGGVAGLLLFIGLGIFFCVRCRHRRRQAERMSQIKRLLSEKKTCQCPH

RFQKTCSPI

Example 5

Construction of Mutant C34-CXCR4 Fusion Proteins

As described previously, genes encoding C34-CXCR4 fusion proteins were constructed, except that rather than using the wild type C34 sequence, mutant C34 peptides were encoded in the fusions. In the "S2" mutants, two of the amino acids were altered (Y638A, S649A), while in the "S10" mutants, ten amino acids have been altered (W628A, W631A, I635A, Y638A, I642A, L645A, S649A, Q652A, N656A, E659A).

The sequences of the S2 and S10 mutants are shown in FIG. 6, which depicts the mutants and the wild type C34 sequences.

Example 6

Effect of C34 Fusions on HIV Entry

To investigate the effect of the C34 CXCR4, CCR5 and CD4 fusions on entrance of HIV into cells, the following assay system involving a canine thymocyte line CF2 luc which contains a reporter construct in which a HIV LTR promoter is fused to a luciferase gene (see Etemad-Moghadam et al, (2000) *J Virol* 74(9) p. 4433) was used. Since the CF2 luc cells are resistant to HIV (they lack the CCR5 and CXCR4 HIV co-receptors, and the HIV receptor CD4), they do not express the luciferase reporter unless the HIV receptor and co-receptors are expressed in the cell.

The CD4 receptor and CCR5 or CXCR4 co-receptors were thus introduced into the cells using expression plasmids. In the presence of the CD4 plus CCR5 combination, luciferase was expressed in the presence of R5 tropic HIV strains. In the presence of the CD4 plus CXCR4 combination, luciferase was expressed in the presence of X4 tropic HIV. Single-cycle HIV infection is sufficient to the HIV that product to activate luciferase in this model system. Briefly, CF2-luc cells were transfected with the C34 fusion constructs in pVAX plasmids. One day after transfection, the cells were re-plated in 24 well plates. The following day, the cells were challenged with virus corresponding to 20 ng p24, and then were incubated for 48 hours at 37° C. Following incubation, the cells were lysed, and luciferase substrate added. Luciferase signal was then measured. In all cases, the cells were co-transfected with a CD4 expression plasmid.

Figure 7:
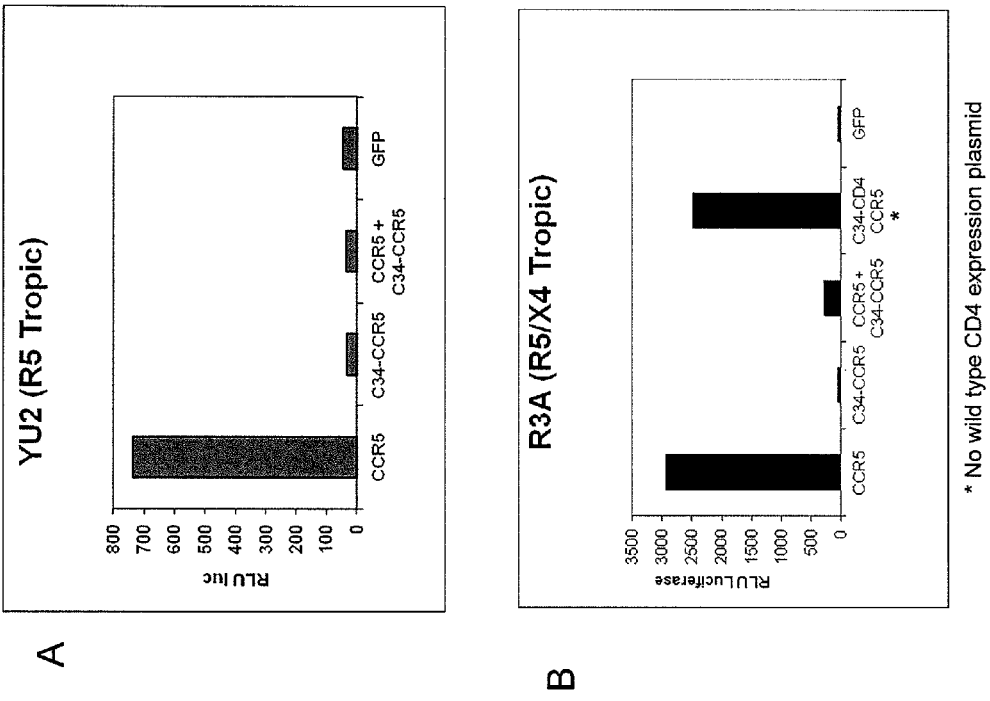
FIG. 7, panels A and B, are graphs depicting luciferase expression in CF2 luc cells driven by a HIV LTR promoter which was expressed only upon entry of HIV into the cells. In all cases except where indicated, the HIV receptor CD4 was supplied by an expression plasmid, and the co-receptors indicated are also supplied as expression vectors.

As shown in FIGS. 7A and 7B, a R5 tropic HIV strain YU2 was able to enter the CD4 plus CCR5 cells, but was blocked from entry in GFP only cells, CD4 plus C34-CCR5 cells as well as in cells that were co-transfected with a CD4 expression plasmid and a 1:1 mixture of wild type CCR5 and C34-CCR5 expression plasmids ("C34-CCR5" and "CCR5+C34-CCR5" respectively). (FIG. 7A).

When the R5/X4 dual tropic HIV strain R3A was used for the challenge (FIG. 7B), as expected, the virus was able to enter CD4 plus CCR5 cells. In cells that had been transfected with a 1:1 mixture of wild type CCR5 and C34-CCR5 expression plasmids ("CCR5+C34-CCR5"), there was a slight increase in entry but generally the virus was blocked. Since these cells did not contain any CXCR4 expression, the CCR5 C34 fusion was sufficient to block entry. In this experiment, the C34-CD4 plus CCR5 containing cells were able to support entry (there was no wild type CD4 expression plasmid in this sample).

Figure 8:
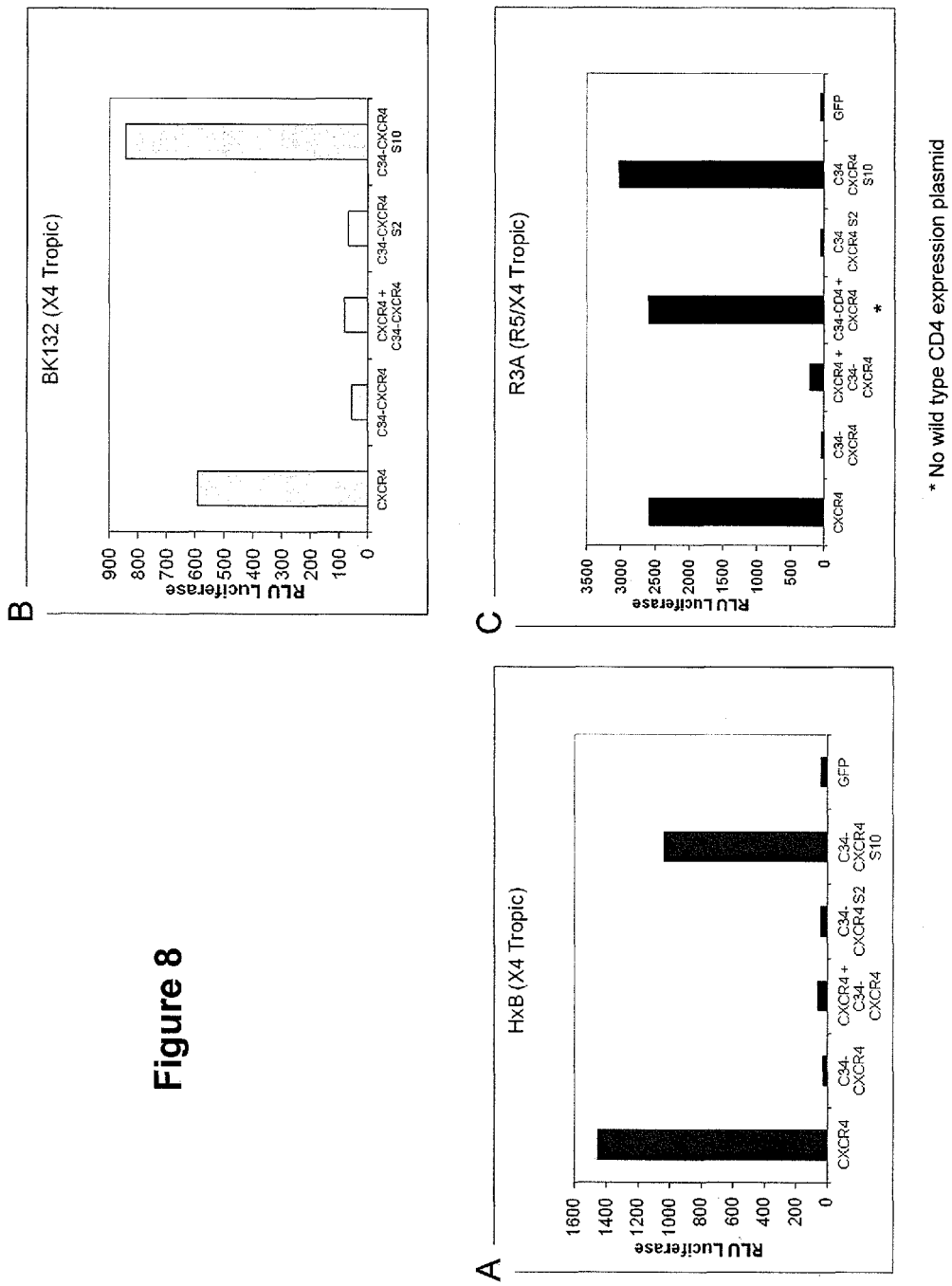
FIG. 8, panels A, B and C, are graphs depicting luciferase expression in CF2luc cells as described above.

Furthermore, as shown in FIG. 8, when the mutant C34 CXCR4 fusion constructs were used, the wild type C34 and the mutant S2 C34 fusion protein containing species were able to block X4 tropic viral entry, but the mutant S10 C34-containing species were not.

Example 7

Titration of C34 Fusion Viral Entry Inhibition

To characterize the ability of the C34 fusion proteins to block viral entry, a series of titration experiments were performed. In these experiments, the CF2 luc system described above was utilized but the cells were transfected with differing ratios of the expression plasmids (from 1:1 up to 100:1) encoding the wild type co-receptor with expression plasmids encoding the C34 fusion co-receptors.

Figure 9:
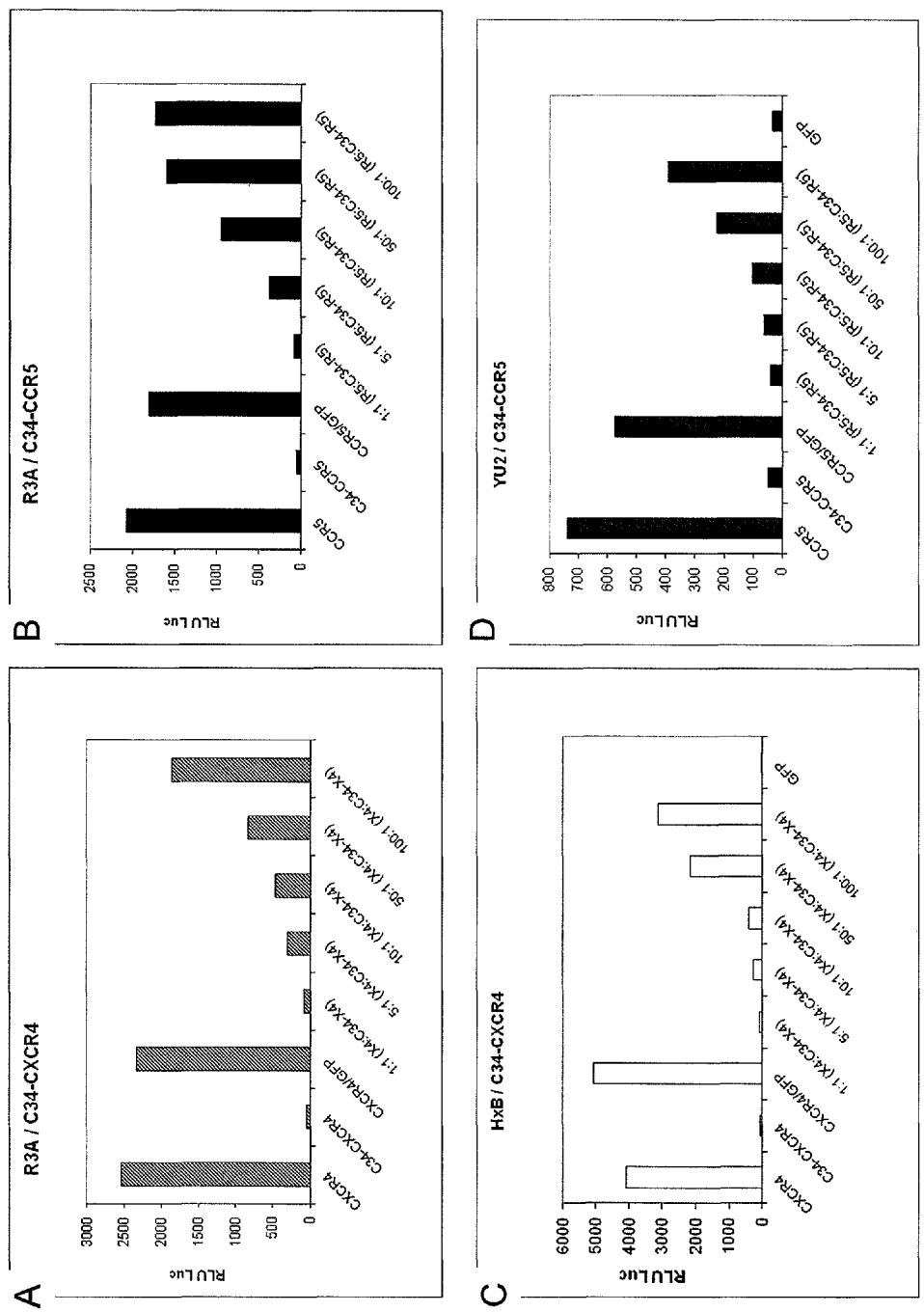
FIG. 9, panels A-D, depict luciferase expression in CF2luc cells as described above in FIGS. 7 and 8. Cells were transfected by a mixture of wild type co-receptor and C34-co-receptor fusion protein. The transfections were done in a range of the two types of expression plasmids from a 1:1 ratio up to a 100:1 ratio.

As shown in FIG. 9, C34 attached to either the CXCR4 protein (FIG. 9A) or the CCR5 protein (FIG. 9B) decreased inhibition of entry for the CCR5/CXCR4 dual tropic HIV (R3A), as the amount of C34 fusion protein expression plasmid was decreased. Similarly, for the CXCR4 tropic HIV strain HxB, a decreased amount of the inhibitory C34-CXCR4 expression plasmid resulted in an increased entry (FIG. 9C). For the CCR5 tropic HIV strain YU2, a decreased amount of the C34-CCR5 expression plasmid also resulted in increased entry of the virus (FIG. 9D).

Example 8

Heterologous Trans Inhibition of HIV Entry

The C34 fusion proteins were also tested to examine if the presence of the C34 peptide on the co-receptor not utilized by a HIV strain inhibit HIV entry. For this experiment, the CF2luc system was again utilized, and the cells were transfected by C34-CXCR4 and C34-CCR5 expression plasmids.

Figure 10:
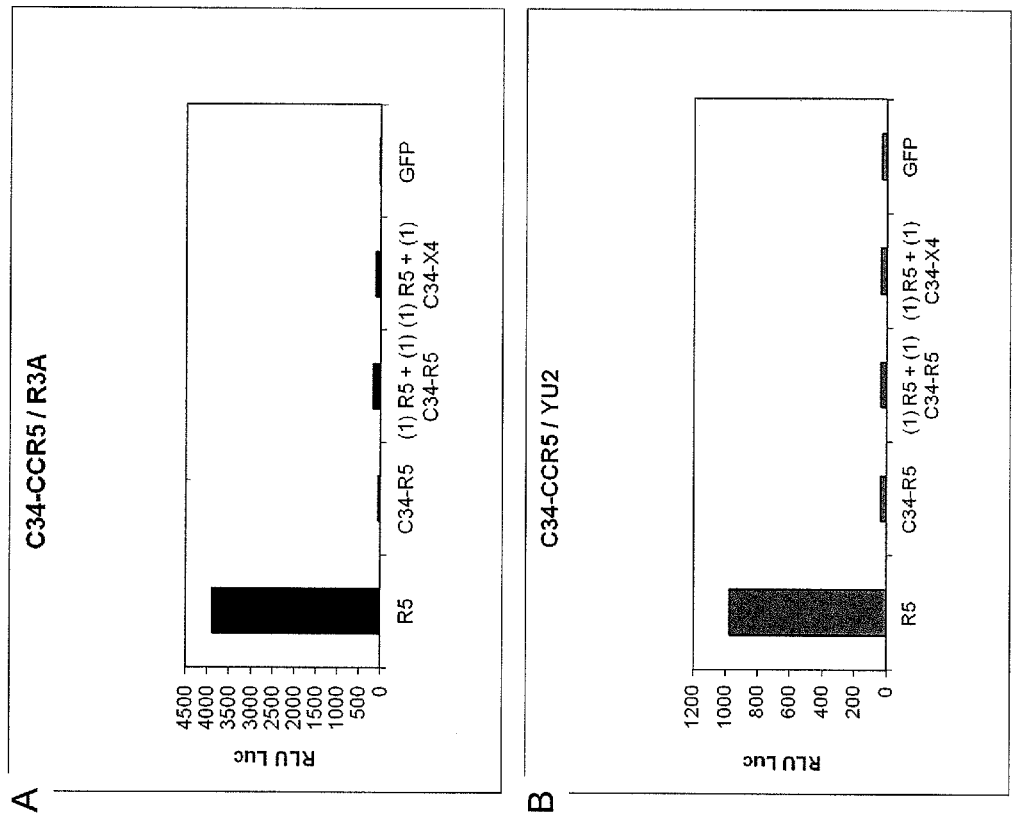
FIG. 10, panels A and B, depict luciferase expression in the CF2luc cells as described above. Inhibition of viral entry was inhibited by the presence of the C34 peptide on the heterologous co-receptor.

As shown in FIG. 10, when the C34 was fused to either the CCR5 co-receptor or the CXCR4 co-receptor, entry of the CXCR4/CCR5 dual tropic HIV strain R3A was inhibited (see FIG. 10A). In this experiment, inhibition of the R3A entry was inhibited when the CF2luc cells were transfected with either C34-CCR5 expression plasmid alone, CCR5 wild type plus C34-CCR5 (1:1 ratio), or CCR5 wild type plus C34-CXCR4 (1:1 ratio). In all cases, CD4 was supplied on an additional expression plasmid. When the CCR5 tropic HIV strain YU2 was used, entry was blocked when the C34 peptide was fused to the CCR5 co-receptor, as well as when wild type CCR5 was supplied with C34-CCR5 fusion or the C34-CXCR4 expression plasmid in a 1:1 ratio (FIG. 10B).

This data demonstrates that the C34 peptide is capable of inhibition when fused to the non-targeted co-receptor.

Example 9

Prevention of Viral Infection

Human CD34+ hematopoietic stem cells are isolated from umbilical cord blood and nucleofected with vectors encoding CXCR4-specific engineered nucleases and a donor construct encoding the C34-CXCR4 fusion as described in Example 1 (see also Holt et al (2010) *Nat. Biotechnol,* 28(8) p. 839). These cells are engrafted into 1 day old NSG mice previously irradiated with low dose (150 cGy) radiation (see Ishikawa et al (2005) *Blood* 106 p. 1565). Engrafted mice are then challenged with CXCR4-tropic HIV when they are 8-12 weeks post transplantation (Holt et al, ibid). Following infection, blood samples are collected from the mice every 2 weeks and analyzed for HIV viral levels, T cell subset ratios and the extent of C34-CXCR4 fusion protein expression. These data are compared to control irradiated NSG mice that have received wild type, non-treated hCD34+. These data demonstrate that while the ratio of CD4/CD8 cells becomes skewed in mice receiving the wild type hCD34+ cells, reflecting changes that occur in human AIDS patients, the mice receiving the C34-CXCR4 fusion expressing CD34+ cells exhibit less of a shift in the CD4:CD8 ration, or maintain the wild type CD4:CD8 ratios.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An isolated mammalian cell comprising an endogenous CD4, CXCR4 or CCR5 HIV receptor or co-receptor gene and an exogenous nucleic acid sequence encoding a fusion protein comprising a C34 peptide fusion inhibitor comprising the amino acid sequence as shown in SEQ ID NO:5 fused in frame to the N-terminal extracellular domain of a CXCR4 or a CCR5 protein, wherein a regulatory sequence is operatively linked to the nucleic acid sequence encoding the fusion protein, wherein the expression of the endogenous HIV receptor or co-receptor gene product in the cell is knocked out, and further wherein the fusion protein is membrane bound and the C34 peptide fusion inhibitor is expressed on the surface of the isolated cell.

2. The cell of claim 1, wherein the exogenous nucleic acid sequence is integrated into an endogenous locus, wherein the endogenous locus is selected from the group consisting of the CD4 locus, the CXCR4 locus, the CCR5 locus and a safe harbor locus.

3. The cell of claim 2, wherein the exogenous nucleic acid sequence is integrated into the endogenous CD4, CXCR4 and CCR5 gene.

4. The cell of claim 3, wherein integration of the exogenous nucleic acid sequence into the endogenous CD4, CXCR4 or CCR5 gene inactivates the endogenous CD4, CXCR4 or CCR5 gene.

5. The cell of claim 1, wherein the expression of the endogenous CD4, CXCR4 or CCR5 HIV receptor or co-receptor gene in the cell is knocked out by a nuclease and the nuclease is selected from the group consisting of one or more zinc finger nucleases, one or more TALENS, one or more homing endonucleases and combinations thereof.

6. The cell of claim 1, wherein the cell is selected from the group consisting of a stem cell, a T-cell, a macrophage, a dendritic cell, a microglia, and an antigen-presenting cell.

7. A method of producing an isolated mammalian cell according to claim 1, the method comprising integrating the exogenous nucleic acid sequence encoding the fusion protein using one or more nucleases into the genome of the mammalian cell.

* * * * *

UNITED STATES PATENT AND TRADEMARK OFFICE
CERTIFICATE OF CORRECTION

Page 1 of 1

PATENT NO. : 9,566,352 B2
APPLICATION NO. : 13/245702
DATED : February 14, 2017
INVENTOR(S) : Michael C. Holmes et al.

It is certified that error appears in the above-identified patent and that said Letters Patent is hereby corrected as shown below:

On the Title Page

Item (66), Related U.S. Application Data, should read:

(66) Provisional application No. 61/404,063, filed on Sep. 27, 2010.

Signed and Sealed this
Sixth Day of June, 2017

Michelle K. Lee
*Director of the United States Patent and Trademark Office*